(12) United States Patent
Siciliano

(10) Patent No.: US 11,957,861 B2
(45) Date of Patent: Apr. 16, 2024

(54) PEN STYLE WIRELESS TATTOO MACHINE, SYSTEM, AND KITS

(71) Applicant: FK IRONS INC., Doral, FL (US)

(72) Inventor: Gaston Siciliano, Pinecrest, FL (US)

(73) Assignee: FK IRONS INC., Doral, FL (US)

( * ) Notice: Subject to any disclaimer, the term of this patent is extended or adjusted under 35 U.S.C. 154(b) by 599 days.

(21) Appl. No.: 17/159,950

(22) Filed: Jan. 27, 2021

(65) Prior Publication Data

US 2021/0244928 A1   Aug. 12, 2021

Related U.S. Application Data

(60) Provisional application No. 62/967,029, filed on Jan. 28, 2020.

(51) Int. Cl.
*A61M 37/00* (2006.01)

(52) U.S. Cl.
CPC . *A61M 37/0076* (2013.01); *A61M 2205/3576* (2013.01); *A61M 2205/80* (2013.01)

(58) Field of Classification Search
CPC ................................................ A61M 37/0076
See application file for complete search history.

(56) References Cited

U.S. PATENT DOCUMENTS

| | | | |
|---|---|---|---|
| 4,204,438 A | 5/1980 | Binaris et al. | |
| 4,914,988 A | 4/1990 | Chang | |
| 5,296,797 A * | 3/1994 | Bartlett | H02J 7/007186 320/133 |
| 5,352,966 A * | 10/1994 | Irons | H02J 7/0013 340/636.15 |
| 5,551,319 A | 9/1996 | Spaulding | |
| 6,550,356 B1 | 4/2003 | Underwood | |
| 7,442,042 B1 | 10/2008 | Lewis | |
| 7,800,343 B2 * | 9/2010 | Aradachi | G01R 31/392 324/426 |

(Continued)

FOREIGN PATENT DOCUMENTS

| | | |
|---|---|---|
| AU | 2019359618 | 5/2020 |
| CA | 3027165 | 12/2017 |

(Continued)

OTHER PUBLICATIONS

World Intellectual Property Organization, "Interational search report and written opinion," issued for International patent application No. PCT/US2021/015314, dated Jun. 3, 2021, document of 11 pages.

*Primary Examiner* — David B. Thomas
(74) *Attorney, Agent, or Firm* — Akerman LLP; Peter A. Chiabotti

(57) ABSTRACT

A wirelessly powered tattoo machine is disclosed, which has a substantially radially symmetric exterior shape for optimal manipulability by a user, and integrated controls for on-device configuration and operation. The power supply component of the machine may be removed, and multiple battery packs may be utilized with a single machine for continuous use. The machine may also be powered by wire and simultaneously operate the machine while charging a connected battery pack. The machine may further include wireless communication with one or more separate devices to operate the machine or control the machine's settings, such as a foot pedal or mobile phone.

20 Claims, 14 Drawing Sheets

(56) References Cited

U.S. PATENT DOCUMENTS

| | | |
|---|---|---|
| 8,228,666 B2 | 7/2012 | Rickard |
| 8,236,021 B2 | 8/2012 | Kluge |
| 8,668,663 B2 | 3/2014 | Kluge |
| 9,254,376 B2 | 2/2016 | Colton |
| 9,433,767 B2 | 9/2016 | Colton |
| 9,750,528 B2 | 9/2017 | Scherkowski |
| 9,827,409 B1 | 11/2017 | Evans et al. |
| 9,931,185 B2 | 4/2018 | Gagliano |
| 9,960,616 B2* | 5/2018 | Kim ............... H02J 7/342 |
| 10,052,469 B2 | 8/2018 | Chan |
| 10,220,195 B2 | 3/2019 | O'Brien |
| 10,220,196 B2 | 3/2019 | Johansson |
| 10,265,482 B2 | 4/2019 | Jones |
| 10,471,246 B1 | 11/2019 | Lipscomb |
| 10,507,314 B2 | 12/2019 | Lee |
| 10,525,245 B2 | 1/2020 | Smith |
| 10,603,429 B2 | 3/2020 | Dantsker |
| 10,898,704 B2* | 1/2021 | Vescovi ............ A61M 37/0084 |
| 10,994,113 B2* | 5/2021 | Johansson ......... A61M 37/0076 |
| 11,173,293 B2* | 11/2021 | Wehinger ......... A61M 37/0076 |
| 2004/0230157 A1 | 11/2004 | Perry |
| 2005/0277973 A1 | 12/2005 | Huang |
| 2008/0300615 A1 | 12/2008 | Colton |
| 2010/0072827 A1 | 3/2010 | Norstrom |
| 2010/0137796 A1 | 6/2010 | Perry |
| 2010/0241151 A1 | 9/2010 | Rickard |
| 2012/0024114 A1 | 2/2012 | Vazquez |
| 2012/0215248 A1 | 8/2012 | Perry |
| 2014/0324089 A1 | 10/2014 | Chan |
| 2015/0025561 A1 | 1/2015 | La Fontaine |
| 2015/0164543 A1 | 6/2015 | Kluge |
| 2015/0194744 A1 | 7/2015 | Slocum |
| 2015/0359559 A1 | 12/2015 | Scherkowski |
| 2015/0367118 A1 | 12/2015 | Scherkowski |
| 2016/0074645 A1 | 3/2016 | Siciliano |
| 2016/0099594 A1* | 4/2016 | Kim ............... H02J 7/0044 |
| | | 320/134 |
| 2016/0121093 A1 | 5/2016 | Fan |
| 2016/0164519 A1 | 6/2016 | Arriaga |
| 2017/0007814 A1 | 1/2017 | Chan |
| 2017/0157382 A1 | 6/2017 | Siciliano |
| 2017/0336870 A1 | 11/2017 | Everett |
| 2017/0354810 A1 | 12/2017 | O'Brien |
| 2018/0000419 A1 | 1/2018 | Rassman |
| 2018/0043146 A1 | 2/2018 | Vescovi |
| 2018/0056054 A1 | 3/2018 | Siciliano |
| 2018/0369553 A1 | 12/2018 | Siciliano |
| 2019/0053465 A1 | 2/2019 | Knight |
| 2019/0076636 A1 | 3/2019 | Lee |
| 2020/0038158 A1 | 2/2020 | Gagliano |
| 2020/0114137 A1 | 4/2020 | Siciliano |

FOREIGN PATENT DOCUMENTS

| | | |
|---|---|---|
| CH | 704096 | 5/2007 |
| CN | 204293679 | 4/2015 |
| CN | 204521979 | 8/2015 |
| CN | 106492344 | 3/2017 |
| CN | 106730312 | 5/2017 |
| CN | 206138576 | 5/2017 |
| CN | 2894616 | 6/2017 |
| CN | 206597222 | 10/2017 |
| CN | 107508966 | 12/2017 |
| CN | 206924246 | 1/2018 |
| CN | 206924247 | 1/2018 |
| CN | 206995603 | 2/2018 |
| CN | 107952167 | 4/2018 |
| CN | 208176733 | 12/2018 |
| EP | 1872823 | 1/2008 |
| EP | 1882492 | 10/2008 |
| EP | 1882491 | 10/2009 |
| EP | 2954927 | 12/2015 |
| EP | 3082938 | 10/2016 |
| ES | 1195334 | 10/2017 |
| KR | 2020003805 | 4/2020 |
| SG | 195416 | 12/2013 |
| WO | 2008146294 | 12/2008 |
| WO | 2011163134 | 12/2011 |
| WO | 2014086342 | 6/2014 |
| WO | 2015156715 | 10/2015 |
| WO | 2017178070 | 10/2017 |
| WO | 2017189606 | 11/2017 |
| WO | 2017194336 | 11/2017 |
| WO | 2019106552 | 6/2019 |
| WO | 2019106553 | 6/2019 |

* cited by examiner

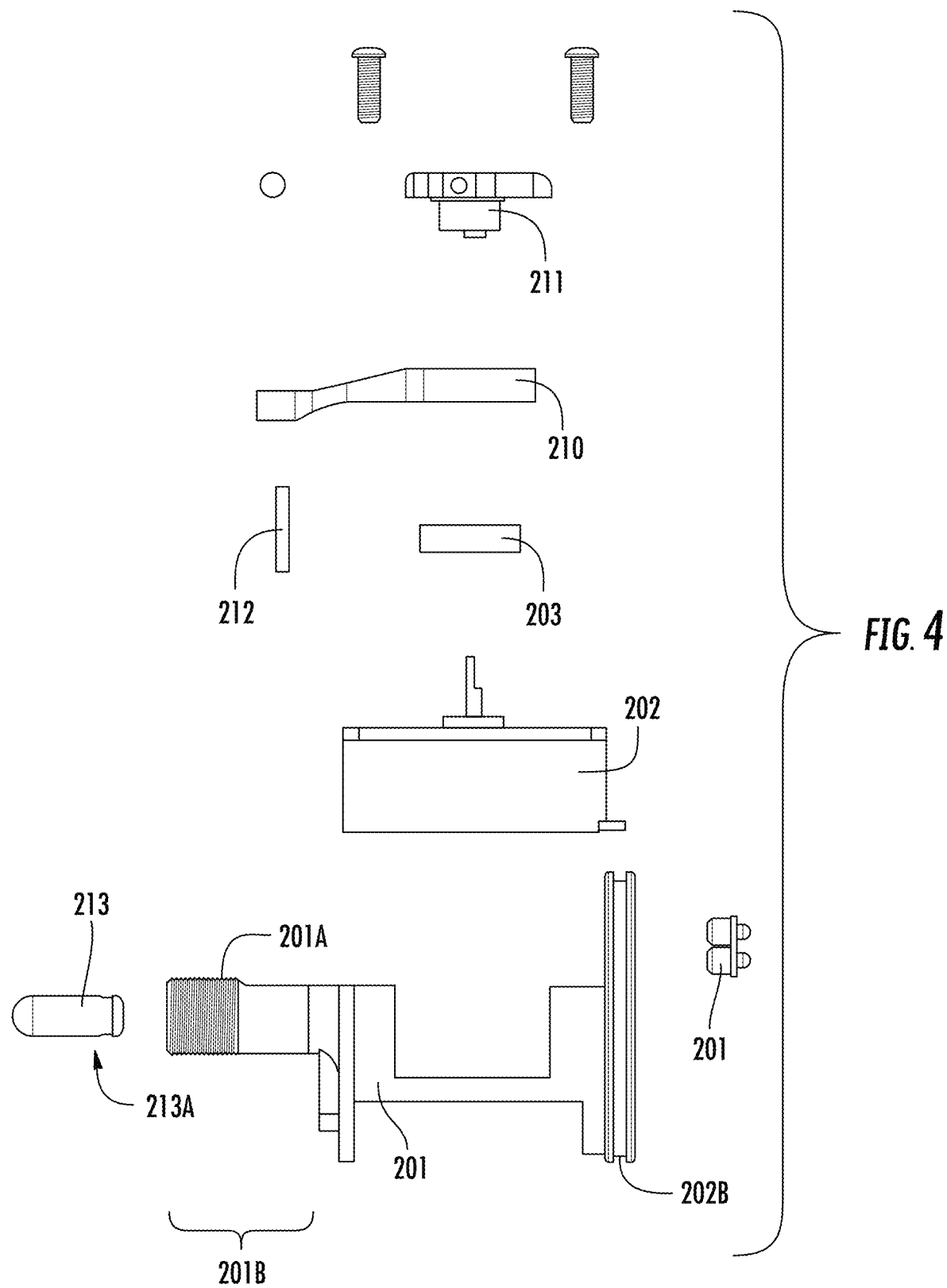

PEN STYLE WIRELESS TATTOO MACHINE, SYSTEM, AND KITS

CROSS REFERENCE TO RELATED APPLICATIONS

This application claims the benefit of and priority to U.S. provisional application No. 62/967,029, filed on Jan. 28, 2020, the disclosure of which is hereby incorporated by reference in its entirety.

FIELD OF THE DISCLOSURE

The disclosure relates generally to the field of mechanical apparatuses, and more particularly, though not exclusively, to a handheld pen-style wireless tattoo or permanent makeup machine, a wireless tattoo machine system, and associated kits. When used with various types of needles, the technology provided by the disclosure can also be useful for implantation of temporary or permanent pigments, compounds, chemicals, large molecules and even cells beneath the skin. The technology provided by the disclosure may also be useful for therapeutic microneedling and stimulation.

BACKGROUND

Tattoo machines generally use electric coils to drive a spring-loaded reciprocating needle structure in order to puncture the upper layers of skin and deposit small amounts of colorant into the skin. Coil-type machines are often bulky, heavy, and cumbersome for the operator (e.g. the tattoo artist, skin therapist, or physician), and typically have an off-balance mass relative to the operator's hand This makes it more difficult for the operator to re-orient the machine by fingertip in the operator's hand during use. Coil machines and existing pen machines are also prone to overheating and vibration, further causing discomfort to the user and thereby shortening the length of time the device can be used over a continuous period. Environmentally for both artist and subject, coil machines and conventional pen-style machines are noisy during operation, thus leading to aural fatigue and shorter tattooing or therapy sessions.

Tattoo artists, cosmetic tattooists, and microneedle therapists desire a machine with superior balance, longer run time, less weight, and which can be operated wirelessly, which thus allows the user to maintain visual focus on and physical contact with the subject receiving the tattoo or therapy—thus reducing the possibility of errors in applying a tattoo or rendering therapy. It is therefore desirable to have a wireless pen-style tattoo or permanent makeup machine whose settings can be adjusted on the fly, wirelessly, by the operator using their voice or a foot pedal.

SUMMARY OF THE DISCLOSURE

The tattoo machines and methods of using the tattoo machines provided by the present disclosure enhance a tattoo artist's mobility in the studio and while applying ink to a customer's skin, and provide detachable battery units to power the tattoo machine. Additionally, certain embodiments of the tattoo machines and methods of using the tattoo machines of the present disclosure eliminate dedicated control devices, and provide direct wireless control between a tattoo machine and a foot switch, and, in certain embodiments, include on-machine controls. Furthermore, the tattoo machines and methods of using the tattoo machines of the present disclosure leverage existing mobile wireless devices to collect information from wireless tattoo machines, and also to control and set the operational parameters of the tattoo machines.

BRIEF DESCRIPTION OF THE DRAWINGS

The following description and the annexed drawings set forth certain illustrative aspects of the disclosure. These aspects are indicative of only some of the various ways in which the principles of the disclosure may be employed, and the present disclosure is intended to include all such aspects and their equivalents. The disclosure can be readily understood by considering the following description in conjunction with the accompanying drawings, in which:

FIG. 4 illustrates an exploded view of an embodiment of a motion translation assembly.

DETAILED DESCRIPTION

Figure 1:
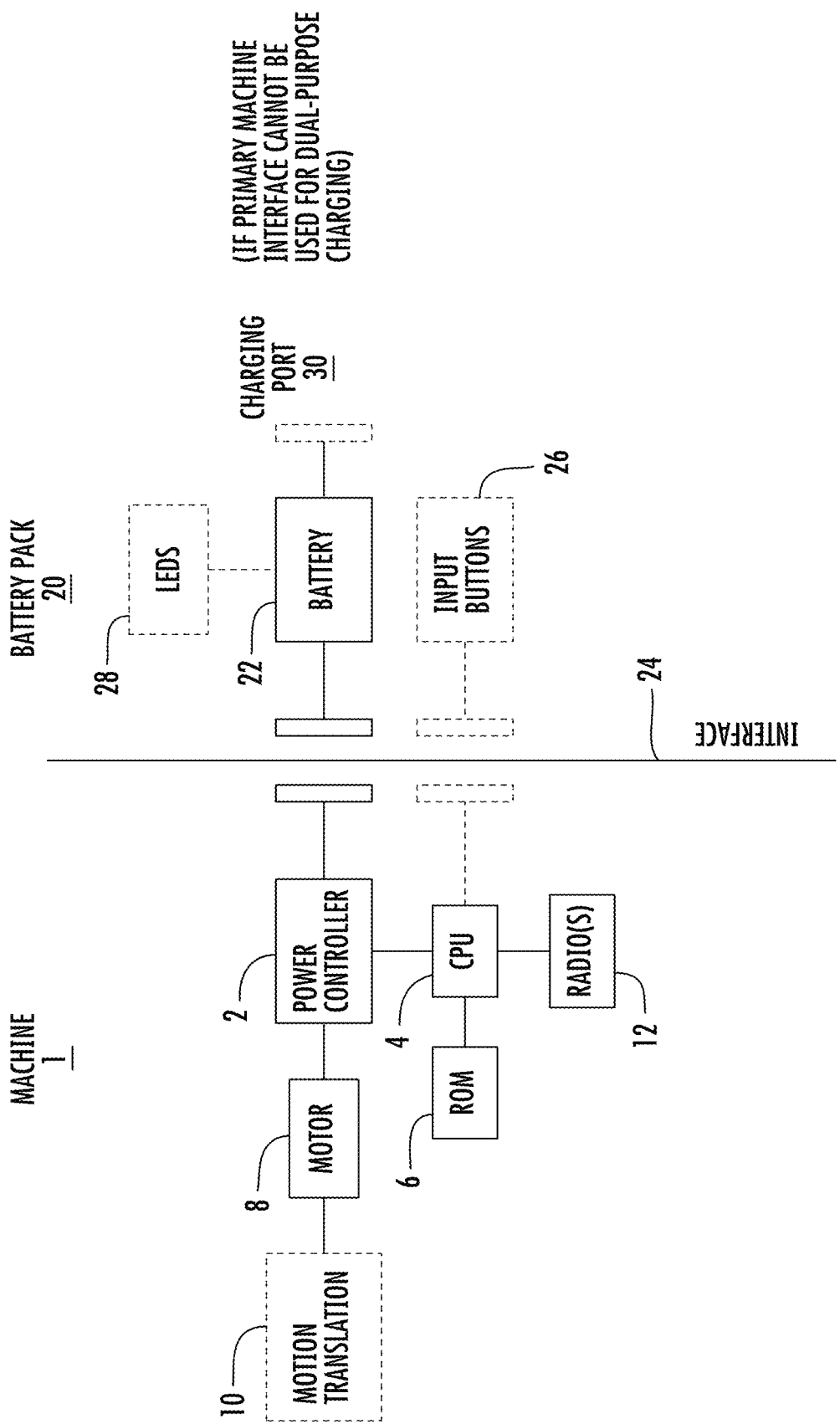
FIG. 1 illustrates a schematic layout of electrical circuitry of an embodiment of a wireless tattoo machine.

In this detailed description, where a document, act, or item of knowledge is referred to or discussed, that reference or discussion is not an admission that the document, act, or item of knowledge or any combination thereof was at the priority date, publicly available, known to the public, part of common general knowledge, or otherwise constitutes prior art under the applicable statutory provision; or is known to be relevant to an attempt to solve any problem with which this disclosure is concerned.

The following detailed description and the appended drawings describe and illustrate various embodiments of the disclosure solely for the purpose of enabling one of ordinary skill in the relevant art to make and use the disclosure. As such, the detailed description and illustration of these embodiments are purely exemplary in nature and are in no way intended to limit the scope of the disclosure, or its protection, in any manner. It should also be understood that the drawings are not to scale and in certain instances details may be omitted, which are not necessary for an understanding of the present disclosure by a skilled practitioner.

The term "at least" followed by a number is used herein to denote the start of a range beginning with that number (which may be a range having an upper limit or no upper limit, depending on the variable being defined). For example, "at least one" means 1, or more than 1. The term "at most" followed by a number is used herein to denote the end of a range ending with that number (which may be a range having one or zero/none as its lower limit, or a range having no lower limit, depending upon the variable being defined). For example, "at most four" means 4 or less than 4, and "at most forty percent" means 40% or less than 40%. When, in this specification, a range is given as "(a first number) to (a second number)" or "(a first number)-(a second number)," that means a range whose lower limit is the first number and whose upper limit is the second number. For example, 25 to 100 mm means a range whose lower limit is 25 mm, and whose upper limit is 100 mm.

The term "mechanical features" is used herein to mean features of a component, mechanical or geometric, which have a functional purpose of attaching or linking that component to one or more other components with compatible or corresponding mechanical features. An example of a mechanical feature is a slot in a component, where said slot is designed to accept a tab from another component and the union of the slot and tab from the two components effectively links, attaches, fixes, and/or locks the components together. The term "mechanical features" refers to, but is not limited to: hooks, hook and loop fasteners, slot and tabs, all male and female fasteners, screws, bolts, nuts, holes that have been tapped, latches, pins, etc.

Disclosed is a wireless tattoo machine powered by a removable battery pack and incorporating remote and on-board controls. The apparatus may accept a variety of needle cartridge designs. The components are arranged in an axial manner along a common central axis and providing an approximately balanced weight distribution radially along the axis, as well as longitudinally from tip to end. The motor may be located at the most frontward position within the apparatus's housing, thereby counter-balancing the weight of the removable battery pack at the rear of the device.

The grip portion is configured to accept various types of needle cartridges. The grip portion is further configured to mechanically couple to the machine housing. A battery unit is removable battery unit that provides wireless power and operability and the battery component of the apparatus maintains the overall axially-symmetric configuration of the machine.

Certain embodiments of the present disclosure may be used for, but are not limited to, the etching of skin, tattooing, micropigmentation, therapeutic micro-needling, scarification, and other therapy or body modification.

A preferred embodiment of a wireless tattoo machine apparatus may comprise a motor housing having an exterior, the exterior having a motor housing perimeter defining a central axis, a motor constrained within an interior portion of the motor housing, the motor having a driveshaft, the driveshaft axis of rotation oriented substantially orthogonal to the central axis, a motion translation assembly dimensioned to fit within the motor housing comprising a cam disk having a cam aperture and an outer cam circumference defining a cam center, the cam aperture being offset a distance from the cam center and dimensioned to accept the driveshaft, whereby the driveshaft rotatably engages the cam disk, a connecting arm having a first end and a second end, the second end having an opening defining an inner arm circumference; and a bearing provided between the outer cam circumference and the inner arm circumference, and a detachable power supply unit, the housing of the power supply unit adapted to reversibly couple to the motor housing rotatably about the central axis and electrically communicate with the motor.

Embodiments of the present disclosure may include components manufactured from materials suitable for human use in medically sterile settings. Such materials are those which are durable, cleanable, or autoclaveable, and are contemplated to be within the scope of the present disclosure. By way of example and not limitation, materials may be stainless steel, tungsten, anodized aluminum, their alloys, or polycarbonates.

The needle unit, also called a needle cartridge, may include one or more needles contained within the cartridge. Needles may be hollow or non-hollow, depending on the application. Other types of implements may be provided within a cartridge other than needles. A pin with blunted tip, micro-scoop, knife or flat blades, needle or pin with a hooked end, or other configuration of a metallic or sterilizable rigid material to achieve the desired goals of a pen-style reciprocating needle machine.

With regard to the motor housing of the disclosed apparatus, its geometric symmetry need not be perfect or absolute. The overall shape of the wireless tattoo machine is configured in a substantially cylindrical unit dimensioned for ease of use in a person's hand.

An object of the disclosure is that the apparatus can be rotated in a user's hand by the hand in which the device is being used (such as by fingertip manipulation) to change the apparatus's needle tip orientation without significantly affecting the feel or without significantly affecting the utility of the device. Thus, non-symmetric features that do not substantially affect or interfere with the goals of reciprocating pen style machine are contemplated by the disclosure. Features which may make the grip or motor housing imperfectly radially symmetric may include ornamental or decorative features, variations in detents to accommodate different grip styles, and so on. The grip may be configured with gripping means. Such gripping means may be recesses, grooves, knurls, or other known surface features or treatments that allow the user to securely grip the apparatus.

It is a further object of a pen-style tattoo machine to fit within a user's hand in a weight-balanced fashion. Hand sizes vary among users, and the mass, configuration, and dimensions of grips may be designed to provide the desired size and weight balance fit tailored for a particular artist's desired "feel". It is contemplated by the disclosure that the housing or grip of the device may be varied to accommodate different size hands, and different weight distribution preferences with or without changing the size or scale of the machine's internal components, housing, or power supply battery pack. Accordingly, the housing or grip portion of the device may range in diameter from about 7 millimeters up to about 45 millimeters. Length of the housing or grip portion of the apparatus may range from 1.5 centimeters to 12 centimeters.

Weight distribution in the pen style machine is a further desirable feature that enhances user comfort and increases precision use of the device. Materials used in certain components may be selected to achieve optimal weight distribution in the machine, end-to-end as between the needle end and the motor end, such that the machine feels balanced while in a user's hand. Similarly, materials may be selected to optimize axial weight distribution. By way of example and not limitation, denser materials may be selected for the grip component of the machine to counter-balance the weight of the motor, battery, or other components opposite from the needle-end of the device so as to achieve an optimal center of gravity or center of mass. Accordingly, the weight of interchangeable grips may range from about 0.9 ounces to about 3 ounces. Incremental balancing weights may also be provided integral with the grip itself, or may be separately removable so as to make a grip's weight customized by an artist to their specific taste. Such weight adjustments may include washers, set screws, or other geometries or configurations of individual weights which can be placed within the grip for desired weight and balance.

A further objective of a pen style machine is to reduce heat and vibration, thus decreasing user fatigue and increasing user comfort. A pen style machine may include a counterbalance to an offset bearing. The mass of the counterbalance may be replaceable or adjusted according to the distance which the offset bearing is from the motor's driveshaft to reduce or eliminate vibration otherwise produced by an unbalanced rotating mass.

The wireless power supply assembly, when mated with the machine housing, forms an integral, sealed unit. Electrical connections between the power supply assembly and motor assembly are thus isolated from the artist's hand and outside environment, reducing potential contamination. Notably, the battery pack may connect with corresponding mating surfaces on the machine housing to allow more than one possible rotational orientation of the power supply assembly relative to the machine housing. A forward portion of the power supply assembly may be partially inserted into a corresponding opening on the machine housing, and rotated about a central axis shared with the machine housing to couple the housing of the power assembly to the machine housing. By way of example and not limitation, the housing of the power supply may be configured to reversibly couple with the machine housing through two, 180-degree alternative mating orientations about a central axis. By way of further example and not limitation, the housing of the power supply may be configured to reversibly couple with the machine housing through three, 120-degree alternative mating orientations about a central axis. Providing more than one mating orientation facilitates fast changing or swapping of a housing of a power supply, or changing between power supply housings.

Alternatively, the housing of the power supply may detentingly engage the machine housing, thus snapping in place by one or more detent-style coupling mechanisms. A lip-and-detent configuration is also contemplated within the disclosure.

As a further alternative, the power supply may threadingly engage the machine housing.

The battery pack may be configured in a variety of shapes depending on the configuration and orientation of the mechanical components of the apparatus. For example, the battery pack may partially surround one or more protrusions from the main assembly or motor housing. This exemplary configuration allows the wireless tattoo machine to employ a longer linear oscillating motor rather than an orthogonally-oriented rotary motor. A corresponding hollow may exist within the battery pack to accept the rearward portion of a linear oscillating motor protruding rearwardly from the motor housing. In this configuration, the battery thus surrounds some or all of a rearward portion of the linear motor when the battery pack is engaged.

The wireless power supply may include an electrical connection for charging the wireless power supply while not in use, or during use. Connection types may include micro USB, USB-C, RCA, or other configurations for delivering power to the battery pack for charging, or for operating the machine. The power supply unit may be charged while the machine is being operated. The power supply may include circuitry to divide power delivered by wire to charge the battery and separately provide power directly to the motor without being supplied from the battery, and thus allow the battery to charge without it having an ongoing demand or load from the motor. Alternatively, the power supply may include circuitry to provision sufficient power to the battery while the battery satisfies the load to the motor directly during charging.

Alternatively, the wireless power supply may include contactless (induction) type means of charging.

A further embodiment may include a direct wire connection on the machine housing, with the circuitry of the machine capable of charging the wireless power supply mated to the machine housing, and also operate the motor.

The wireless power supply may further include visual information feedback to a user. Such information can be provided through light emitting diodes, either directly from the diode, or presented more broadly with greater surface area or visibility, such as through diffusers, light pipes, fiber optics, or similar light-directing materials and shapes. As one example, the wireless power supply may include a band about its circumference that emits light so that the user may see the visual feedback information irrespective of how the user may happen to be holding the tattoo machine.

Specific colors or sequences of flashes of light can provide information about the state of the battery pack, the motor, the overall machine, or combinations of sub-components. Specific information may include the level of charge of the battery, the charging status, the voltage being delivered to the motor, life remaining in the battery, or time required to full charge.

The wireless tattoo machine includes circuitry to allow the apparatus to communicate with various remote devices. The apparatus may be in communication wirelessly directly with a foot switch. A foot pedal may provide on/off signals to the wireless tattoo machine, thus allowing the user to maintain visual and hand-contact with the apparatus, the subject receiving the tattoo, or both. In operation, the wireless tattoo machine voltage may be adjusted directly by one or more buttons on the power supply assembly, on the machine housing, or both. Thus, in one configuration, a wireless tattoo machine system may include the apparatus, needle cartridge, and foot switch without the need for an intermediary wireless or wired control unit. The artist controls the parameters of the machine directly on the machine itself, and starts and stops the machine by wireless foot pedal in communication with the machine or battery pack. A direct wireless connection between the wireless tattoo machine and a foot pedal may reduce latency from activation of the foot pedal by the operator to the wireless tattoo machine without the need for an intermediary control unit which coordinates communication between the foot switch and battery pack or machine.

In another embodiment, a wireless tattoo machine may be operated and adjusted without any separate control unit or foot switch. Turning the device on and off and adjusting the frequency of reciprocation of the needle may all be achieved through a simplified button interface. In such an embodiment, circuitry within the wireless tattoo machine may have preconfigured voltage increments that may be adjusted by a user to achieve the desired needle frequency. Changes in voltage output from the power supply assembly may be approximately linear between the highest and lowest settings, or changes may be incremental.

Operational parameters of the wireless tattoo machine may be adjusted through a single button by pre-defined sequences. For example and not by way of limitation, a single button may be provided on the exterior of the apparatus. A user may turn the apparatus on and off through a short press-and-release of that button. The voltage output from the power supply may be increased through a separate pattern, such as a press-release-press-hold sequence. In response to receiving such a press-release-press-hold signal from the input button, circuitry within the wireless tattoo machine may slowly increase the voltage output by pre-defined increments. The user would continue to hold the button depressed until the machine reaches the desired level of output voltage, and then release the button. Similarly, a different pattern may be used to decrease the voltage output, such as a press-hold sequence wherein the user would continue to hold the button depressed until the machine reaches the desired level of voltage output, and then release the button.

In a press-and-hold change to the voltage, circuitry provided within the wireless tattoo machine may accelerate the rate of change from voltage to voltage rather than linearly. Such accelerated rate of change in voltage can be useful when an artist needs to significantly adjust the voltage. By utilizing an accelerated rate of change of voltage, a user reduces the amount of time the adjustment button must be held before reaching the desired voltage. A lower rate of change at the beginning of an adjustment hold period would allow the user to fine-tune the voltage after quickly adjusting the machine to the approximate desired voltage after a longer hold and more rapid voltage change.

The wireless tattoo machine may include more than one button. In another embodiment, there may be three buttons, a dedicated on-off button, a dedicated voltage-up button, and a dedicated voltage-down button. Alternatively, in that 3-button embodiment, the wireless tattoo machine may include circuitry that allows for combinations of buttons to be depressed simultaneously to change settings or configure the apparatus. For example, and not by way of limitation, simultaneously depressing both the voltage-up and voltage-down buttons may allow the wireless tattoo machine to pair or connect with another wireless device.

The wireless tattoo machine may include one or more light sources, such as an LED, to provide a user with visual feedback about the state of the machine. States of the wireless tattoo machine may include its voltage setting, or the amount of battery life remaining. A single LED may be provided on the exterior of the battery housing, capable of producing a plurality of colors. Various colors of the LED may correspond to pre-defined voltage settings, such that when the user selects particular voltage on the wireless tattoo machine, the LED may emit a continuous source of a specific color, or flashes. Various colors and flash combinations may represent different voltage settings. Similarly, different colors and sequence of flashes may provide a user with other information about the wireless tattoo machine. By way of example and not limitation, a constant red-color light emitted from the LED may indicate a completely drained battery. Another state may include a green flashing LED at rate of flashing different from the flashing green light associated with a voltage setting. Such fast-paced green flashing LED may indicate a near-full charge of the battery.

The wireless tattoo machine control circuitry may also include electrical safety features. Such safety features may include overcurrent protection to prevent the flow of electricity from the battery to the motor under certain conditions. Such overcurrent protection may be triggered when the motor has completely failed, seized, or is in the initial stages of failure. Overcurrent protection may also be triggered when a motor bearing has failed or has reached a sufficient level of frictional resistance impeding the rotation of the motor.

The wireless tattoo machine may include accessories comprising a kit. Such accessories may include disposable sleeves or membranes dimensioned to surround and cover the wireless tattoo machine, thus isolating the machine from a user's hand. The sleeves or membrane material may be transparent or translucent to allow the user to maintain visual contact with the machine's onboard light emitters which may provide a user with information or feedback about the machine's state. Other accessories may include tattoo needle cartridges, or other cartridges, such as skin stimulation needles.

The wireless tattoo machine may communicate wirelessly with a mobile phone or other mobile device, such as a tablet or general purpose computer. Software provided on the mobile device may be configured to send to and receive control signals from the wireless tattoo machine. Control software on the mobile device may further incorporate connections to the mobile device's microphone and speaker to provide the user with touchless voice-based control of the wireless tattoo machine.

The electronic circuitry provided within the wireless tattoo machine may include more than one transceiver or radio, thereby allowing the apparatus to communicate with more than one other device. For example, the apparatus may be simultaneously connected to a wireless foot switch, and a mobile phone.

The electronic circuitry of the machine may also include various sensors, such as accelerometers, thermometers, gyroscopes, hygrometers, GPS, and other sensors for monitoring the state of the tattoo machine, the battery, the motor, or of the machine's use by the user. Such information provided by the sensors may be stored in memory included as part of the circuitry. Particular kinds of information that might be monitored and stored include the operational parameters of the device, device identification information (such as serial number), length of the machine's operation in a given tattoo session, overall hours of operation, temperature, shock or impacts, or GPS location.

The circuitry may also be adapted to broadcast a unique identifier to facilitate communication with other wireless devices. Near-field communications (NFC) are but one example.

As can be appreciated from the foregoing variety of configuration alternatives, the single wireless tattoo apparatus may be operated completely independent of any other control device or unit, together with a mobile device, together with a traditional tattoo machine control unit, together with a wireless foot switch, or various combinations of foot switch, control unit, and mobile device—depending on a user's desired hardware configuration preferences, desired control and operation of the apparatus, and set up.

The motor or control circuitry may have a positional memory of the rotor relative to the stator such that the motor, when not operated, has a resting position wherein the drive pin is at its most retracted position. Such a resting position obviates the need for a spring to ensure withdrawal of the needle into the cartridge housing when the apparatus is not being operated. The positional memory may be achieved by magnetic design or solenoid within the motor, or through stored memory and signals from the power supply to the motor. Similarly, the motor may have a positional memory where the needle remains stationary in a fully extended position, allowing the operator to inspect the condition of the needle.

The motor tray may include features customized to prevent an end user from accessing the motion translation assembly, the motor, the motor tray, or other components contained within the motor housing. Such security features may include one or more recesses capable of accepting a corresponding custom tool. In one embodiment, the letters "F L U X-F L U X-" may be recessed from a face of a nut at one end of the motor housing and oriented substantially circumferentially about the central axis, the nut adapted to contain the components within the motor housing.

The battery pack may include security features to prevent the user from accessing the components contained within the battery housing.

The interior of the grip may have an internally threaded portion. These threads are configured to accept the externally threaded portion of the housing. This threaded engagement allows for the needle depth to be adjusted. To shorten the needle depth, a user rotates the grip relative to the housing in one direction. In order to lengthen the needle depth, the user may turn the grip (relative to the housing) in the opposite direction. This rotation of the grip relative to the housing changes the distance between the grip-cartridge combination and the housing. In this way, the needle depth may be adjusted from zero up to approximately four millimeters.

The pen style machine may optionally include a means for identifying the range of the needle throw, such as having numbers or other markings on the housing with a corresponding constrained viewing area which indicates needle throw based on the relative spacing between the grip and the housing.

Methods of using a wireless tattoo machine are also contemplated by the disclosure. In one embodiment, a method of stimulating an innate healing response of a person's skin is disclosed, comprising the steps of providing a substantially radially symmetric microneedling machine, providing a patient, identifying a target area of skin to be stimulated on the person's body, and operating the microneedling machine to stimulate the patient's skin for a period of time sufficient to impart a therapeutic effect. In another embodiment, a method of introducing an inert substance into the skin of a person or animal comprising the steps of providing a substantially radially symmetric microneedling machine, providing a substance capable of being accepted into an aperture of a hollow microneedle, identifying a target area of skin into which the substance will be implanted, introducing the substance into the microneedle, and operating the microneedling machine on the skin to implant the substance to the desired depth. A cellular therapy, biologic therapy, small molecule drug, vaccine, or other medically therapeutic substance may also be introduced into a patient's skin to produce a therapeutic result.

Referring now to the figures in general, and to FIG. 1 in particular, an embodiment of the present disclosure in the form of a pen style wireless tattoo machine apparatus 1 is disclosed showing the arrangement of electrical components comprising the tattoo machine 1. Notably, the machine 1 may include any of the features and functionality described in the present disclosure and is not limited to the features and functionality shown in FIG. 1. The machine 1 may include one or more of the following components: a power controller 2, a CPU 4, a memory 6, a motor 8, a motion translation assembly 10, a communication device 12, and a battery pack 20, which may include a battery 22, a machine-interface 24, input button(s) 26, LEDs 28, and a charging port 30. In certain embodiments, the machine 1 may include any number of display screens and/or interfaces. For example, the machine 1 may include a LCD display, an organic LED display, another type of LED display, an electroluminescent display, AMOLED display, plasma display, quantum dot display, thin-film transistor-based displays, and/or any other type of display. In this embodiment, the control circuitry for controlling the machine 1 may be contained within the machine housing of the tattoo machine 1, while the battery pack 20 includes a battery 22 and a machine-interface 24 for electrical communication of the battery 22 to the power controller 2 contained within the machine housing of the tattoo machine 1. In certain embodiments, the CPU 4 may regulate the flow of electricity from the battery 22 to the motor 8 via the power controller 2. In certain embodiments, the CPU 4 may be an electronic hardware processor device, and, in certain embodiments, may comprise hardware, software, or a combination of both hardware and software. In certain embodiments, the CPU 4 may be configured to execute instructions, such as instructions that may be stored in memory 6, to perform any one or more of the operations of the tattoo machine 1. In electrical communication with the CPU 4 is memory 6 (e.g. ROM), and a communication device 12 for communicating wirelessly with other devices. In certain embodiments, the memory 6 may comprise hardware, software, or a combination of hardware and software. The memory 6 may be configured to be any type of memory (e.g. RAM, flash, volatile, non-volatile, etc.), however, in certain embodiments, the memory 6 may be ROM-style memory (i.e read-only memory) which includes instructions that are fixed in memory and are not alterable. Instructions stored in the memory 6 may be accessed and executed by the CPU 4 to perform various operative functionality of the tattoo machine 1. For example, the instructions may be executed by the CPU 4 to adjust the amount of electrical power provided to the various components of the tattoo machine 1 via the power controller 2, to process sensor data obtained via optional sensors of the tattoo machine 1, monitor usage of the tattoo machine 1, transmit data to the communication device 12 for transmission to remote devices and/or systems, perform any other operations, or a combination thereof.

The communication device 12 of the tattoo machine 1 may be a radio device, a transceiver, a wireless module, a wireless chip (e.g. Bluetooth chip, near-field communications chip, a cellular chip, etc.), an infrared communication device, any type of communication device, or a combination thereof. In certain embodiments, the communication device 12 may communicate utilizing any type of communications protocol including, but not limited to, infrared-based protocols, Bluetooth-based protocols, short-range wireless protocols, long-range wireless protocols, wifi, ISM, DECT, 6LoWPAN, Thread, NFC, Zigbee, Z-wave, cellular protocols, any type of radio technology, any type of communications protocol, or a combination thereof. The communication device 12 may be utilized by the tattoo machine 1 to communicate with other devices, such as, but not limited to, the mobile device 2000, the foot switch 4000, a user device, any other device, or a combination thereof. Additionally, the communication device 12 may be utilized by the tattoo machine 1 to communicate with other components of the tattoo machine 1 itself, such as, but not limited to, the CPU 4, the memory 6, any other components of the communication devices 12, or a combination thereof. The communication device 12, for example, may be configured to receive processed sensor data from the CPU 4, which may then be transmitted via the communication device 12 to the mobile device 2000 for further processing and/or analysis. The communication device 12 may also receive information from the mobile device 200, foot switch 400, and/or other remote devices, which may then be forwarded to the CPU 4 for processing and/or the memory 6 for storage.

In certain embodiments, the communication device 12 may receive control signals from the foot switch 4000, the mobile device 2000, and/or other remote devices that may be utilized to control one or more components of the tattoo machine 1 itself. As an example, a user of the mobile device 200, such as via an application executing on the mobile device 200, may enter a command into the application to control the operation of the tattoo machine 1. As illustrative examples, the user may enter a command in the mobile device 2000 to activate the motor 8 of the tattoo machine 1, to specify the amount of electrical power to be delivered to the motor 8, to specify an amount of motion for the motion translation assembly 10 to apply to a needle of a needle cartridge connected to the tattoo machine 1, to activate and/or deactivate sensors of the tattoo machine 1 to gather sensor data associated with the tattoo machine 1, to deactivate the tattoo machine 1, to modify a type of motion of the motion translation assembly 10, to adjust an amount of voltage delivered to the components of the tattoo machine 1 via the battery 22, to indicate which data generated by the tattoo machine 1 to be processed by the CPU 4 and/or stored by the memory 6, to adjust a needle depth of a needle of a needle cartridge attached to the tattoo machine 1, to adjust an amount of force applied to the needle, to adjust a speed at which the needle moves, perform any operation to be conducted by the tattoo machine 1, or a combination thereof.

The motion translation assembly 10 of the tattoo machine 1 may be utilized to provide motion to a tattoo needle of a cartridge attached to the motion translation assembly 10 of the tattoo machine 1. The power controller 2 and CPU 4 may regulate the amount of electrical power from the battery 22 of the battery pack 20 that is delivered to the motor 8, which can, in turn, be utilized to regulate the amount of motion (i.e. mechanical energy) generated by the motor 8 that is to be imparted to the needle cartridge. The mechanical energy provided by the motion translation assembly 10 via the motor 8 may be utilized by the tattoo machine 1 to move a needle of the needle cartridge so that a user can effectively deposit ink onto/into a user's skin and/or to perform therapeutic treatments on a user's skin.

Optionally, in certain embodiments, the battery pack 20 may include a light source (e.g. LEDs 28) or a Display screen (e.g. LCD) for providing visual feedback to a user. For example, the LEDs 28 may be configured to output light so as to indicate the state of the battery pack 20, the state of the motor 8, the state of the tattoo machine 1 itself, and/or the states of other components of the tattoo machine 1. In certain embodiments, the LEDs may also be utilized to indicate the level of charge of the battery 22, the charging status of the battery 22, the voltage being delivered to the motor 8, the remaining in the battery 22, time required to fully charge the battery 22, whether the tattoo machine 1 is overheating, whether components of the tattoo machine are failing or about to fail, whether sensors of the tattoo machine 1 are activated and/or deactivated, whether control signals are being received by the tattoo machine 1 from remote devices such as the foot switch 400 and/or mobile device 200, and/or any other suitable information. The LEDs may also be configured to flash in certain patterns and/or sequences to indicate various states of the tattoo machine 1 as well. In certain embodiments, the color of the light emitted by the LEDs 28 may change depending on the state of the tattoo machine 1. The battery pack 20 may also optionally include a charging port 30 separate from the machine-facing interface 24, which may be utilized to charge the battery 22 of the battery pack 20. In certain embodiments, an end of a cord of an electrical plug may be positioned into the charging port 30 and the electrical plug may be plugged into an electrical outlet to facilitate the charging of the battery 22 of the battery pack 20. The battery pack 20 may also include one or more input buttons 26 configured for electrical communication with the circuitry contained within the machine housing of the tattoo machine 1. In certain embodiments, the input buttons 26 may be utilized to activate and/or deactivate the tattoo machine 1, adjust an amount of voltage to be delivered to the motor 8, activate and/or deactivate sensors of the tattoo machine 1, perform any other operations of the tattoo machine 1, or a combination thereof.

Figure 2:
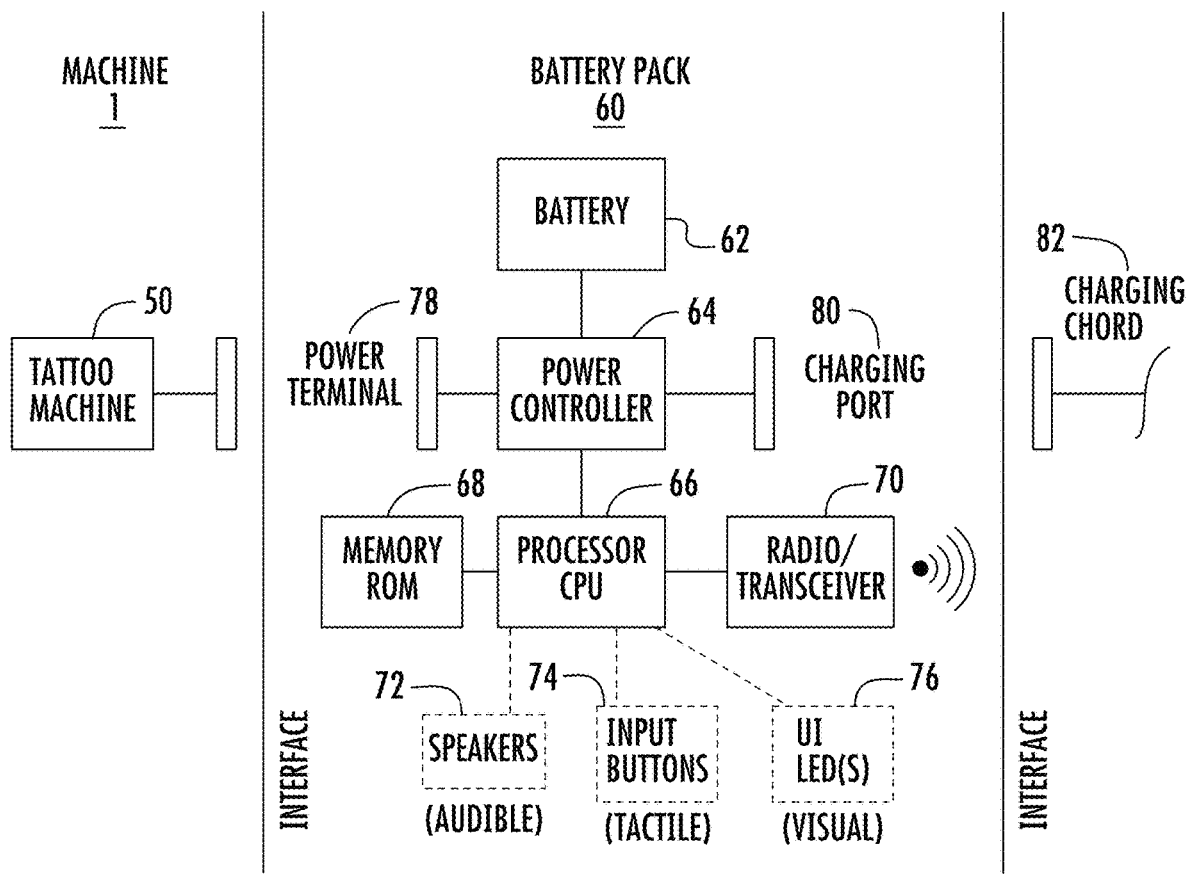
FIG. 2 illustrates another embodiment of a wireless tattoo machine and system.

FIG. 2 shows another embodiment of a wireless tattoo machine 50 in which the control circuitry is provided within the battery pack 60. In certain embodiments, the components of tattoo machine 50 may operate in a similar fashion as the corresponding components in tattoo machine 1. The tattoo machine 50 may be powered by a battery pack 60, such as via power terminal 78. In the embodiment shown in FIG. 2, the battery pack 60 may include a battery 62, a power controller 64, a CPU 66, a memory 68, a communication device 70, speakers 72, input buttons 74 for controlling the tattoo machine 50, user interface LEDs 76 for outputting state information associated with the tattoo machine 50, a power terminal 78, and/or a charging port 80. FIG. 2 also includes a charging cord 82, which may be plugged into the charging port 80 of the battery pack 60 to charge the battery 62. The control circuitry of the battery pack 60 may include a processor 66, memory 68, the battery 62, and the communication device (e.g. transceiver, radio, wireless chip, communications module, and/or other communication device). The circuitry may further include a power terminal 78 and a charging port 80. The power terminal 78 may deliver power to the tattoo machine 50 via the battery pack 60. The power terminal 78 may be utilized to provide power generated by the battery 62 to the tattoo machine 50 so as to cause a motion translation assembly of the tattoo machine 50 to move a needle of the tattoo machine 50. The speakers 72 may be configured to output sound, such as audio generated by a user of the tattoo machine 50 and/or by a device controlling the tattoo machine 50. In certain embodiments, the speakers 72 may also include microphones for receiving voice commands for controlling the operative functions of the tattoo machine 50. The communication device 70 may be in communication with the communication device 89 contained as part of circuitry within a foot switch 85, as shown in FIG. 2A.

Figure 2A:
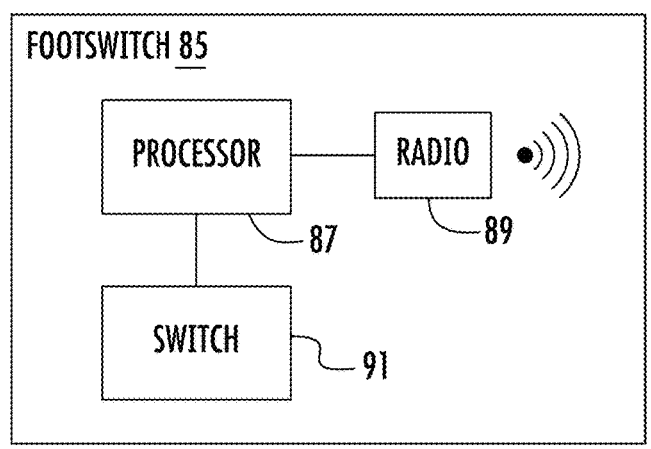
FIG. 2A illustrates a wireless foot switch embodiment as part of a wireless tattoo machine system.

The foot switch 85 of FIG. 2A may be utilized to control the tattoo machine 50 (or other tattoo machines described herein). The switch 91 of the foot switch 85 may be toggled on or off to activate or deactivate the foot switch 85. The foot switch 85 may also include a processor 87, a communication device 89, and/or any other components, such as a power source, sensors, memories, and/or other suitable componentry. In certain embodiments, the switch 91 and the processor 87 may be utilized to generate control signals for controlling the tattoo machine 50. For example, the switch 91 and/or processor 87 may be utilized to generate control signals for activating and/or deactivating the tattoo machine 50, pairing and/or unpairing the foot switch 85 with the tattoo machine 50 either directly or through a bridge connection device, such as a power supply, adjusting a rate at which a needle of a needle cartridge reciprocates and/or moves, activating and/or deactivating sensors of the tattoo machine 50, adjusting an amount of voltage delivered to the motor of the tattoo machine 50, activate and/or deactivate the speakers 72, adjust the type of actions that the input buttons 74 are configured to do, any other controls, or a combination thereof. Control signals generated via the switch 91 and/or processor 87 may be provided to the communication device 89, which may be any type of communication device including, but not limited to, a radio device, a transceiver, a wireless module, a wireless chip (e.g. Bluetooth chip, near-field communications chip, a cellular chip, etc.), an infrared communication device, any type of communication device, or a combination thereof. The communication device 89 may then transmit the control signals wirelessly to the communication device of the tattoo machine 50 so as to control the tattoo machine 50 as desired. The transmitted signal may be specific to the action required or can be general and interpreted by the tattoo machine 50 based on context or other method of interpreting. As an illustrative example, if the tattoo machine 50 is in an "ON" state, a tap on a button (or other input mechanism) of the footswitch 4000 may cause a control signal to cause the tattoo machine 50 to turn "OFF". The footswitch 4000 can then be tapped again sending the same control signal to cause the tattoo machine 50 to turn back to an "ON" state.

Figure 3:
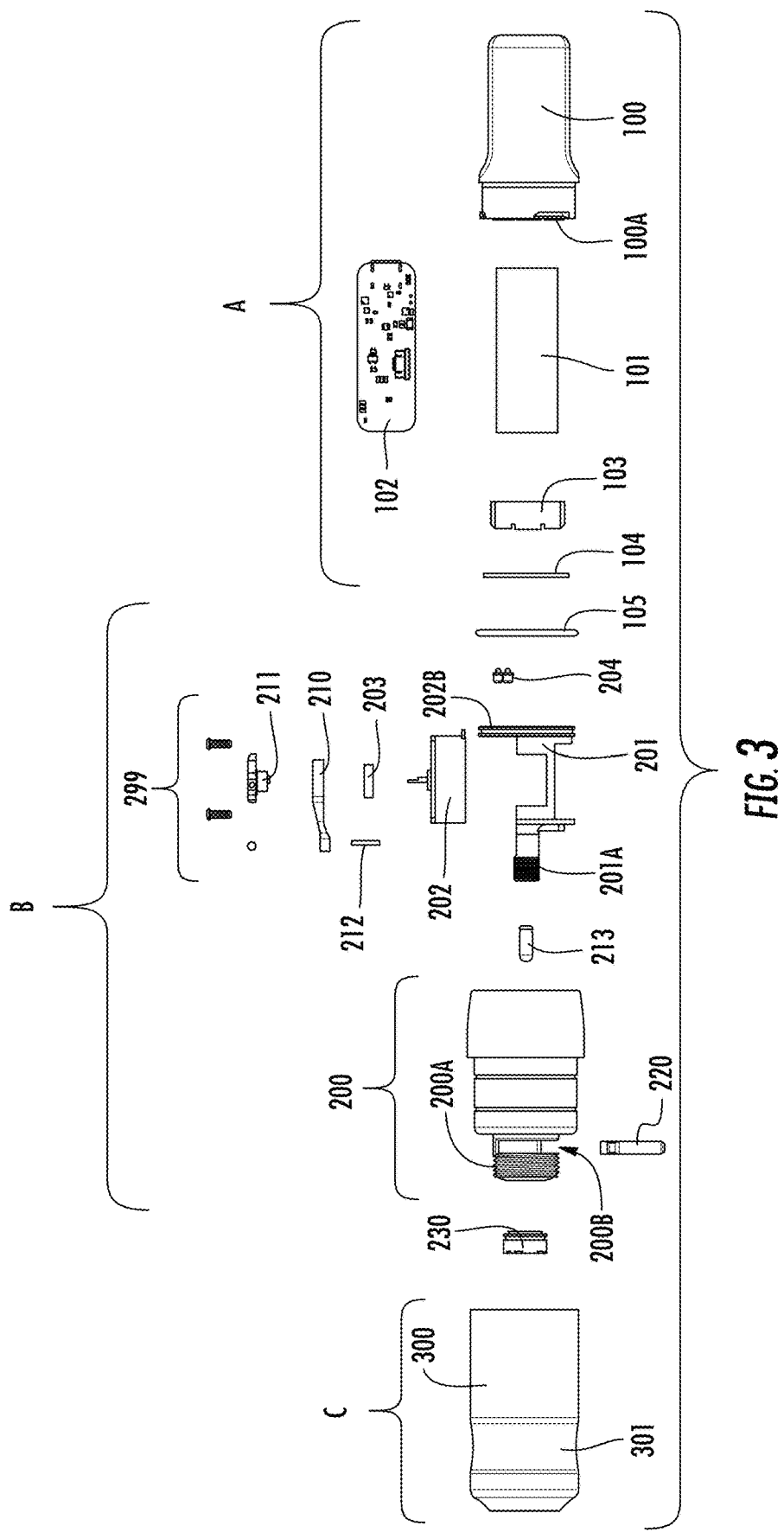
FIG. 3 illustrates an exploded view of an embodiment of a wireless tattoo machine.
Figure 5A:
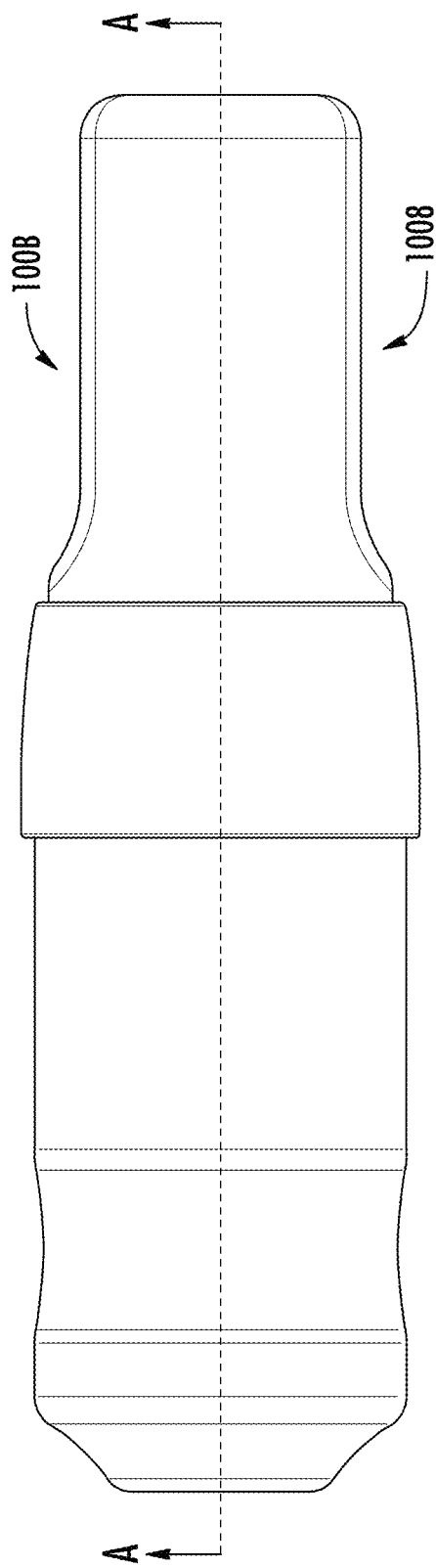
FIG. 5A illustrates a side view of an embodiment of a wireless tattoo machine.
Figure 5B:
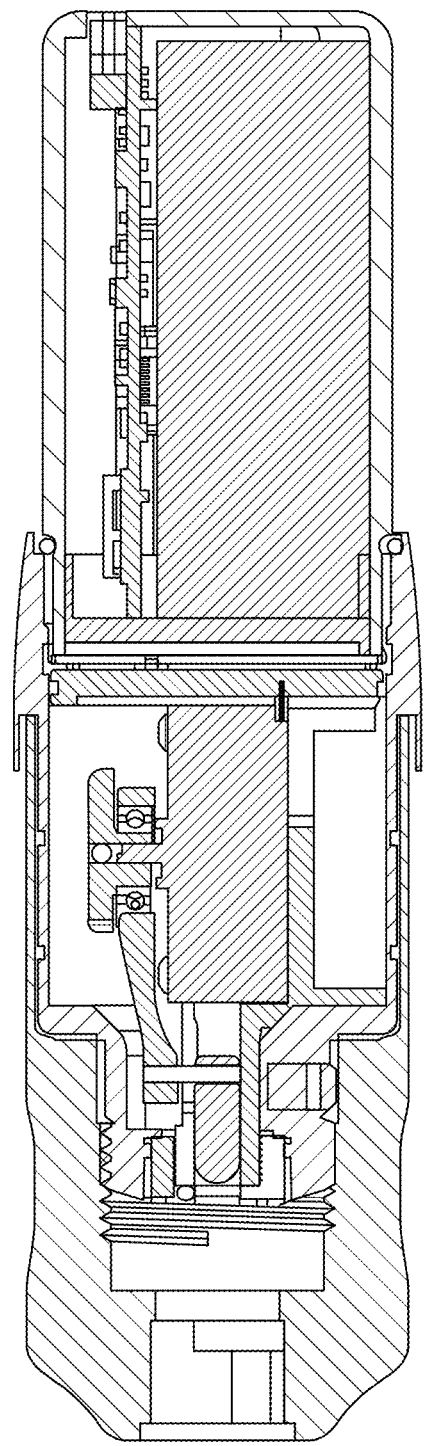
FIG. 5B illustrates a cross-sectional view of the embodiment of the wireless tattoo machine provided in FIG. 5A.
Figure 6A:
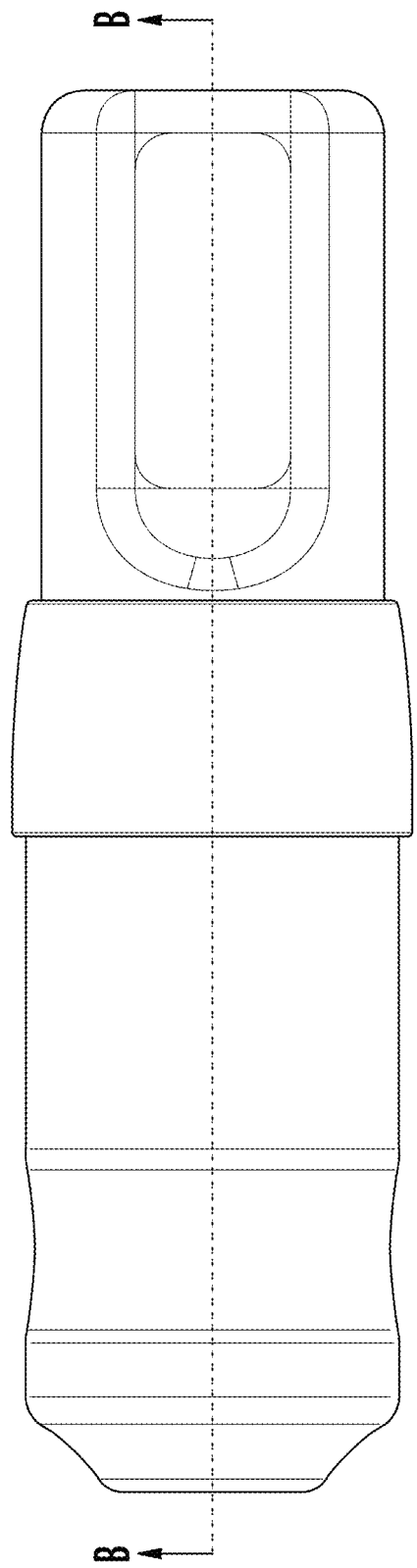
FIG. 6A illustrates another side view of another embodiment of a wireless tattoo machine.
Figure 6B:
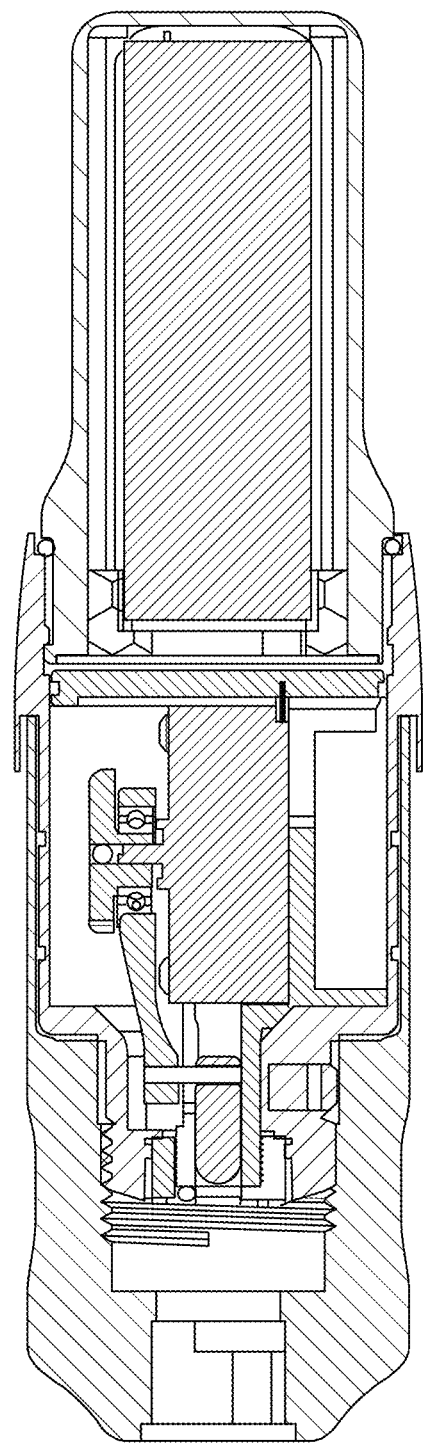
FIG. 6B illustrates another cross-sectional view of the embodiment of the wireless tattoo machine shown in FIG. 6A.
Figure 7A:
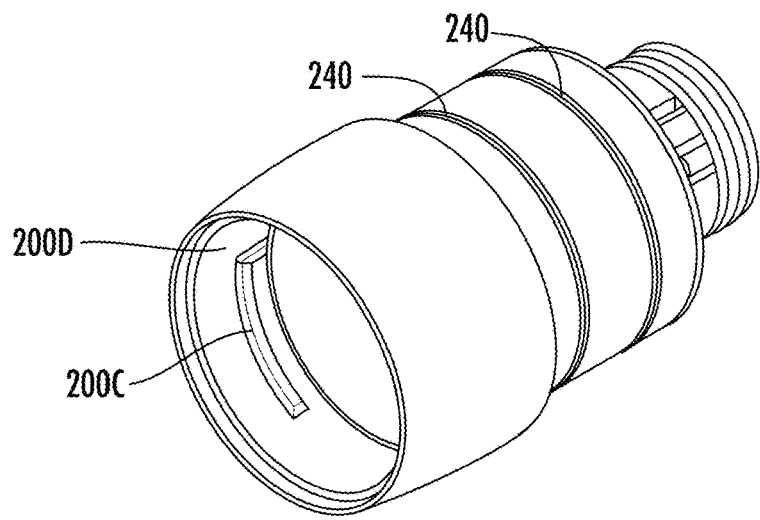
FIG. 7A illustrates a perspective view of a motor housing of an embodiment of a wireless tattoo machine.
Figure 7B:
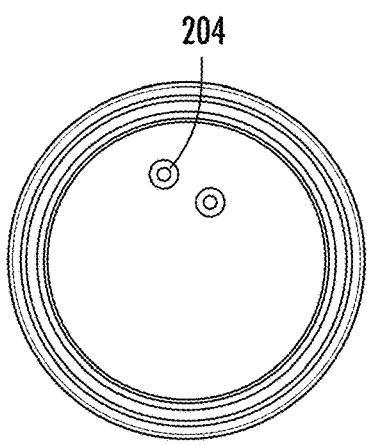
FIG. 7B illustrates a bottom view of the motor of FIG. 7A.
Figure 7C:
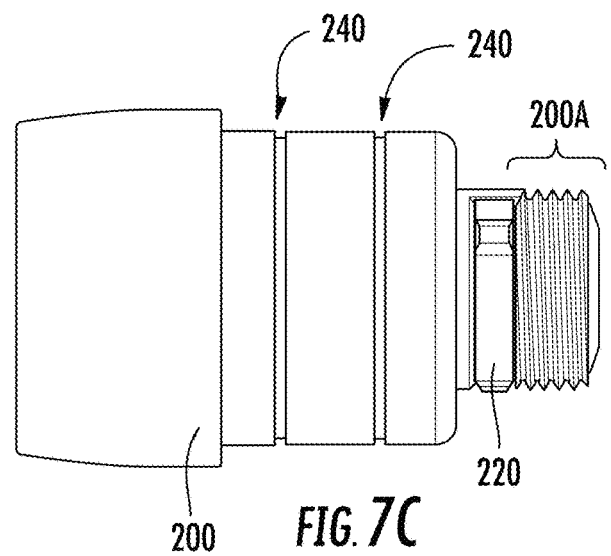
FIG. 7C illustrates side view of the motor of FIG. 7A.
Figure 7D:
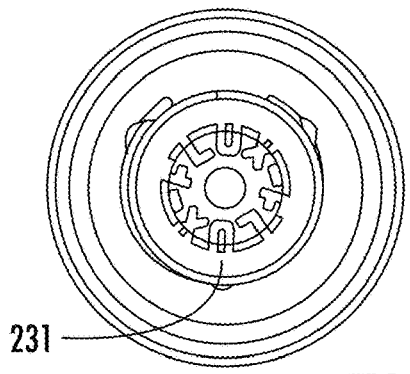
FIG. 7D illustrates the top view illustrating a front end of the motor of FIG. 7A.

FIG. 3 shows an exploded view of an embodiment of a wireless tattoo machine. The battery pack A includes a battery housing 100, a rechargeable battery 101, electronic circuitry on a printed circuit board 102, an end cap 103, a circular contact board 104, and a gasket 105. The battery housing may include twist-lock mating features 100A. The machine main unit B includes a motor housing 200 and a motion translation assembly 299. The motor housing includes a threaded forward portion 200A, a slot 200B dimension to slottedly accept a ratchet disc 220. The motion translation assembly includes a motor tray 201, which has a forward threaded portion 201A and a rearward portion having a slot 202B to accept a gasket. The motion translation assembly also includes a motor 202, the output driveshaft of the motor rotationally engaged by a bearing 203, the bearing fitted between the drive shaft and a connecting arm 210 via a cam disk 211, such that the motor driveshaft rotationally engages in oscillating fashion the connecting arm 210. The connecting arm has a forward portion adapted to engage a drivepin 213 via a connecting pin 212. The motor is in electrical communication with one or more contacts 204, which align with corresponding contacts on the circular contact board 104. The machine main unit has a security nut 230 having internal threads adapted to threadingly engage to the corresponding threads on the forward portion 201A of the motor tray. A grip C is provided, having a substantially circular radially symmetric exterior 300, and finger gripping portion 301. The wireless tattoo machine, when assembled, has a substantially cylindrical shape along a central axis.

Turning now to FIG. 4, shows a close-up exploded view of an embodiment of the motion translation assembly.

In FIGS. 5A, 5B, 6A and 6B, an embodiment of a wireless tattoo machine is depicted in cross-sectional view. Section A-A defines the central axis about which the exterior of the wireless tattoo machine has a substantially radially symmetric shape. The battery housing of a wireless tattoo machine may include one or more partially flat faces 100B. Section B-B of FIG. 6A defines the cross-section shown in FIG. 6B With reference now to FIGS. 7A-7D, the motor housing 200 includes three twist-lock mating features 200C dimension to correspond to twist-lock features of the battery pack such that the battery pack housing may be reversibly rotationally coupled to the motor housing. The twist lock mating feature or raised, partially circumferential internal ridge 200C with a lock end 200D. The housing 200 can have one or more raised, partially circumferential internal ridge 200C, such as three spaced equidistant from each other around the circumference of the mating end of housing 200. The rearward battery-facing portion of the motor housing includes exposed spring-loaded contacts 204. A forward portion of the motor housing may include one or more grooves 240 dimension to constrain a gasket between the motor housing and a grip. The motor housing includes a threaded forward portion 200A to threadingly engage a grip. The motor housing includes a ratchet disk 220 frictionally constrained within an area rearward of the threaded portion 200A. The forward portion of the motor housing includes a security nut tooling face 231.

Figure 8:
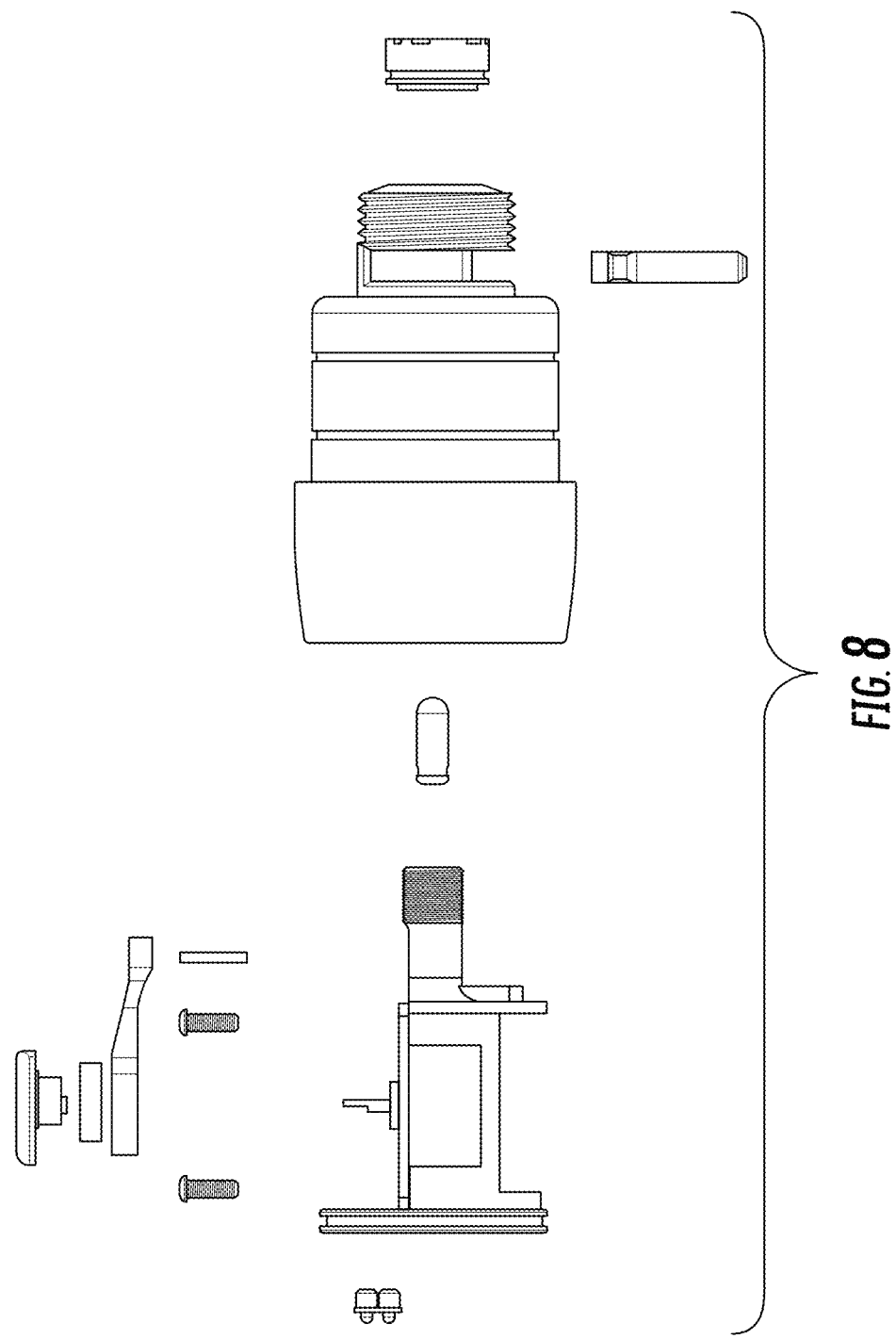
FIG. 8 illustrates an exploded view of an embodiment of a motion translation assembly and motor housing.
Figure 9A:
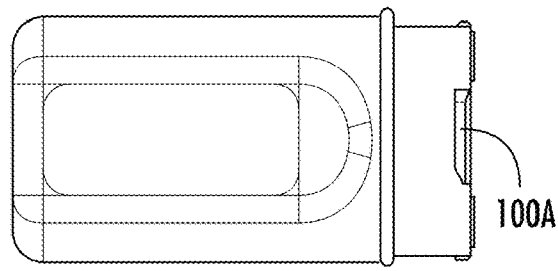
FIGS. 9A-9E illustrate several views of a battery housing of an embodiment of a wireless tattoo machine.
Figure 9B:
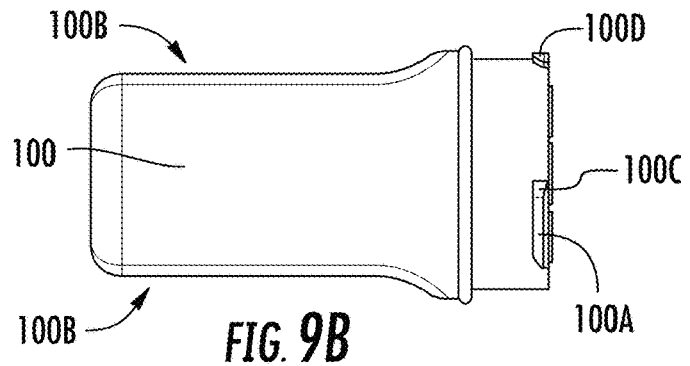
Figure 9C:
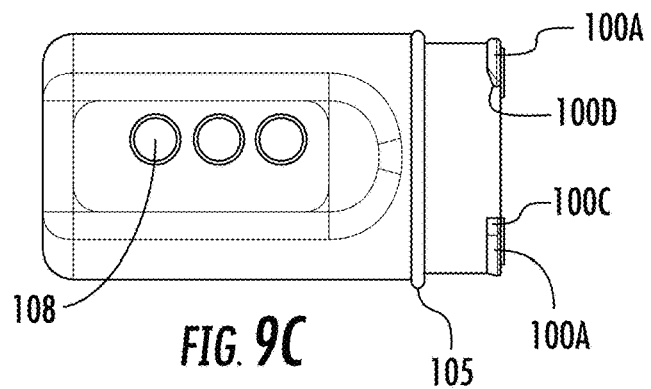
Figure 9D:
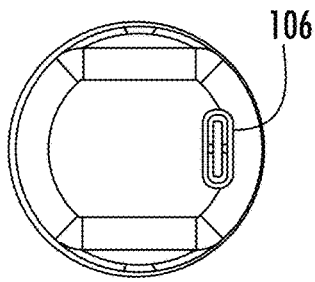
Figure 9E:
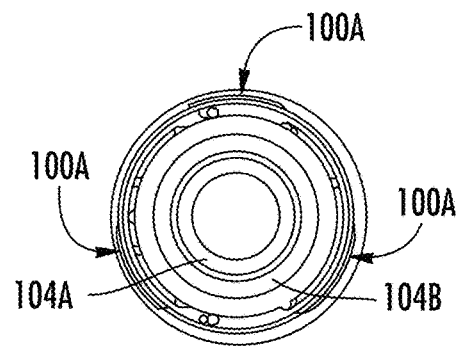
Figure 10A:
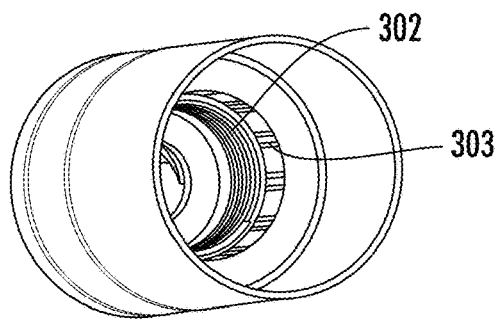
FIGS. 10A-10E illustrate several views of a grip of a wireless tattoo machine.
Figure 10B:
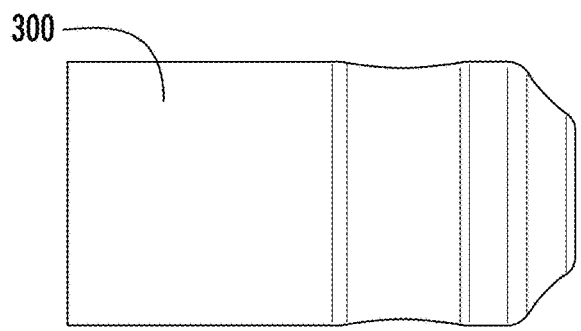
Figure 10C:
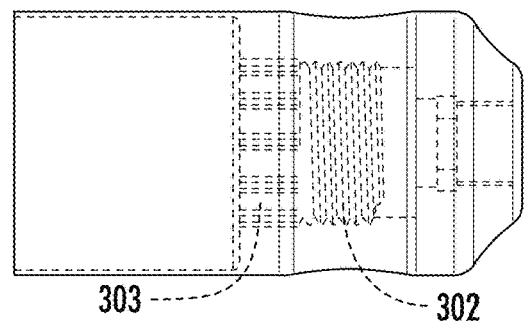
Figure 10D:
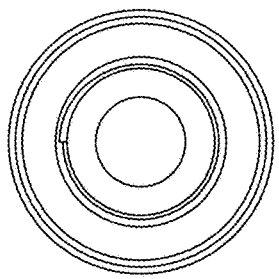
Figure 10E:
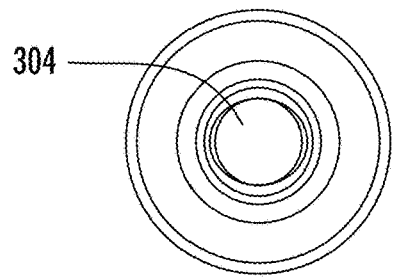
Figure 11A:
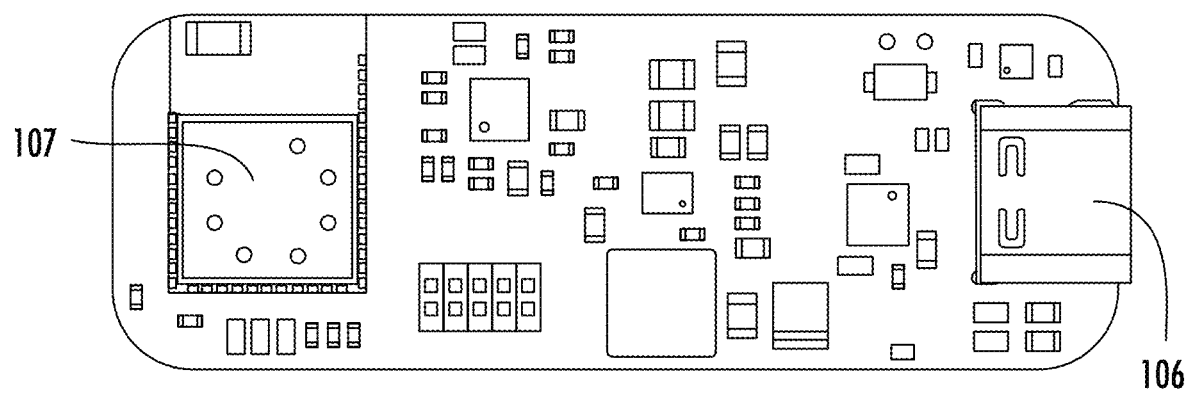
FIGS. 11A-11D illustrate several views of a printed circuit board of a wireless tattoo machine.
Figure 11B:
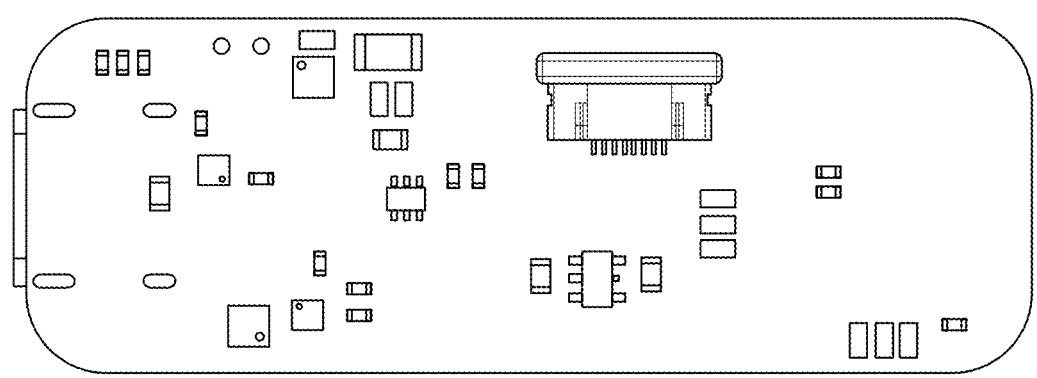
Figure 11C:
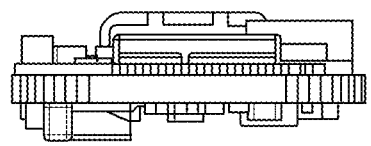
Figure 11D:
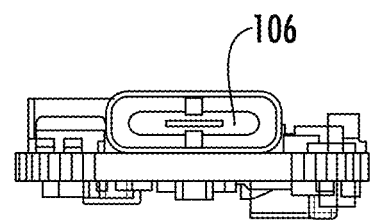

FIG. 8 shows another exploded view of the motor housing and motion translation assembly.

FIGS. 9A-E illustrate a battery pack housing of an embodiment of a wireless tattoo machine. The battery housing 100 includes partially flat surfaces 100B to enhance user grasping of the battery pack and enhance twist engagement and removal of the battery pack from the main unit. The battery housing 100 also may have twist-lock mating features or partial circumferential ridges 100A to facilitate connection of the battery housing 100 to the main unit of the wireless tattoo machine. The housing 100 can have one or more, such as three, partial circumferential ridges 100A spaced equidistant from each other around the circumference of the mating end of housing 100. Each partial circumferential ridge 100A extends outward or radially from the longitudinal axis of housing 100 to form a ridge. Each partial circumferential ridge 100A can have an angled or beveled end 100D that tapers the angle of one end of the partial circumferential ridge 100A both circumferentially and along the longitudinal axis of the housing 100 away from the mating end. At the opposing end a partial circumferential ridge 100A, an not tapered or not beveled end 100C can be provided. On the opposite end the circumferential ridge 100A During assembly, the battery housing 100 can be inserted into the mating end of the motor housing 200 such that the partial circumferential ridge 100A advances internally past the partially circumferential internal ridge 200C, at which point, a user can twist or rotate battery housing 100, motor housing 200, or both, and such that the partial circumferential ridge 100A slides within a slot created internally to each partially circumferential internal ridge 200C and locks in place. The angled or beveled end 100D can be the lead end of each partial circumferential ridge 100A to help ensure that each partial circumferential ridge 100A is guided internal to the partially circumferential internal ridge 200C and away from the mating end of motor housing 200. With such an arrangement, the battery housing 100 removable locks to the motor housing 200. One or more buttons 108 are provided on the exterior of the battery housing 100, and are in electrical communication with the electronic circuitry contained within the wireless tattoo machine. A USB-C charging port 106 on the rearward portion of the battery housing is in electrical communication with the electronic circuitry contained within the wireless tattoo machine. The circular board has a first circular contact 104A, and a second circular contact 104B. The circular contacts are arranged to electronically engage the corresponding contacts on the main unit.

FIGS. 10A-E illustrate an embodiment of a wireless tattoo machine grip 300. The grip 300 includes a plurality of grooves 303 aligned co-axially to the central axis, and dimensioned to detentingly engage the corresponding detents of the ratchet disk. Internal threads 302 translate the grip onto the corresponding threaded forward portion of the main unit. The grip has a forward end having an opening 304 dimensioned to accept a tattoo needle cartridge.

FIGS. 11A-D illustrate an embodiment of electronic circuitry contained within a wireless tattoo machine. Electronic circuitry includes transceiver 107, and a USB-C port 106.

Figure 12:
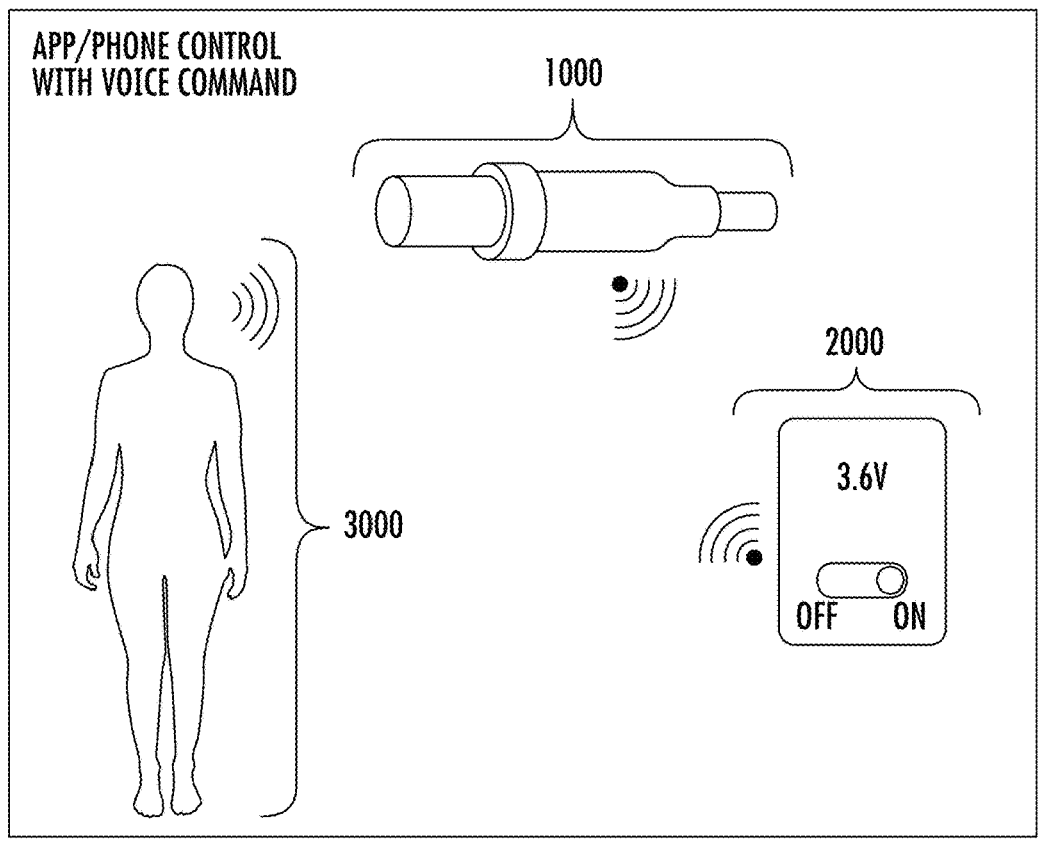
FIG. 12 illustrates a wireless relationship of an embodiment of a wireless tattoo machine, a wireless mobile device, and a user.

FIG. 12 illustrates an embodiment of a wireless tattoo machine system in which a user 3000 orally controls a wireless tattoo machine 1000 through a mobile device 2000 without any physical contact with the mobile device. The mobile device 2000 is in wireless communication with the tattoo machine 1000, and has software designed to accept the user's voice commands, translate those commands into one or more signals, and transmit those signals wirelessly to the tattoo machine, thereby controlling the operation of the tattoo machine by voice. This communication may be voice commands directly to the mobile device or can pass through any number of intermediary devices, including, but not limited to smart speakers, smart watches Bluetooth or other wired or wireless headsets.

Figure 13:
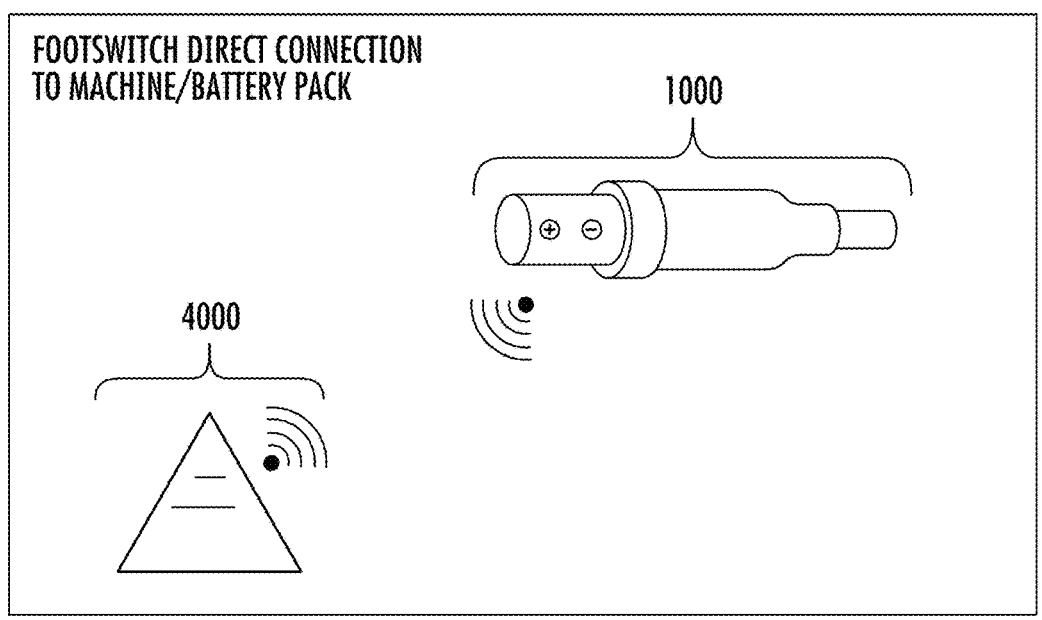
FIG. 13 illustrates a wireless relationship of an embodiment of a wireless tattoo machine and wireless foot switch.

FIG. 13 illustrates yet another embodiment of a wireless tattoo machine system in which a foot switch 4000 is in direct wireless communication with a tattoo machine 1000.

Figure 14:
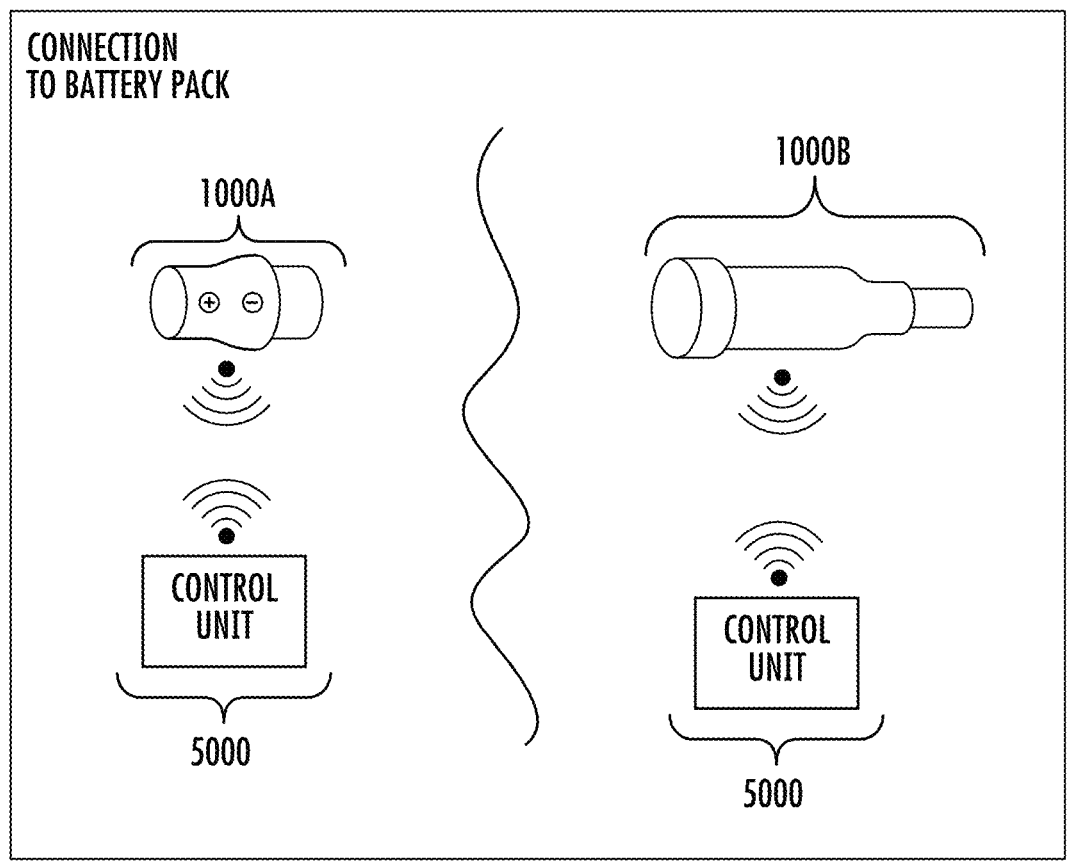
FIG. 14 illustrates a wireless relationship of an embodiment of a wireless tattoo machine and wireless tattoo machine control unit.

FIG. 14 illustrates a further embodiment of a wireless tattoo machine system in which a wireless control unit 5000 is configured to be in direct wireless communication with a battery pack 1000A. FIG. 14 also illustrates how an embodiment of the present disclosure may include electronic circuitry directly within the main unit of the machine rather than within the battery pack, and how a wireless control unit 5000 may be in wireless communication with the main unit 1000B separate from the battery pack 1000A.

FIGS. 12, 13, and 14 generally illustrate how the wireless tattoo machine may be configured to (a) operate independently and only with a wireless foot switch, (b) operate completely independently of any communication with any other control device and be operated and configured directly through buttons provided on the battery pack or machine housing, (c) operate in conjunction with general purpose wireless devices, such as a phone or tablet via an application on the device configured to accept user input through the device's touchscreen, (d) operate in conjunction with the general purpose wireless device, such as a phone or tablet, via an application on the device configured to accept user input through voice commands, or (e) operate in conjunction with dedicated wireless control units configured specifically for operating a wireless tattoo machine.

A wireless battery pack charging station is also contemplated within the disclosure. The charging station may include a battery pack capable of charging one or more wireless battery packs. Electronic circuitry provided within the wireless battery pack charging station may be configured to identify specific battery packs. The circuitry may also be configured to provide rapid charging or pre-defined charging sequences to achieve optimal balance between fast charge time and achieving a full charge in the battery pack. The wireless charging station may also be configured to charge the battery packs conductively or by induction. The charging station may include one or more mating features capable of reversibly coupling with one or more battery packs.

The wireless charging station may include accessories comprising a kit. Such accessories may include disposable sleeves or membranes dimensioned to surround and cover the wireless tattoo machine, thus isolating the machine from a user's hand. The sleeves or membrane material may be transparent or translucent to allow the user to maintain visual contact with the machine's onboard light emitters which may provide a user with information or feedback about the machine's state. Other accessories may include tattoo needle cartridges, or other cartridges, such as skin stimulation needles. The wireless battery pack charging station may also be combined with a control unit, such that the control unit is powered by the onboard battery, and individual battery packs may be recharged from the onboard battery. In this way, a tattoo artist has a completely wireless set up not requiring any dedicated power source for operating a wireless tattoo machine over the course of the tattoo session, or even over the course of an entire day. The battery pack charging station may be designed to include sufficient milliamp hours to charge three or more wireless tattoo machine battery packs, and thereby provide continuous uninterrupted wireless tattooing system for a tattoo artist. The charging station may optionally include USB charging ports for powering additional components, such as a mobile device.

Figure 15:
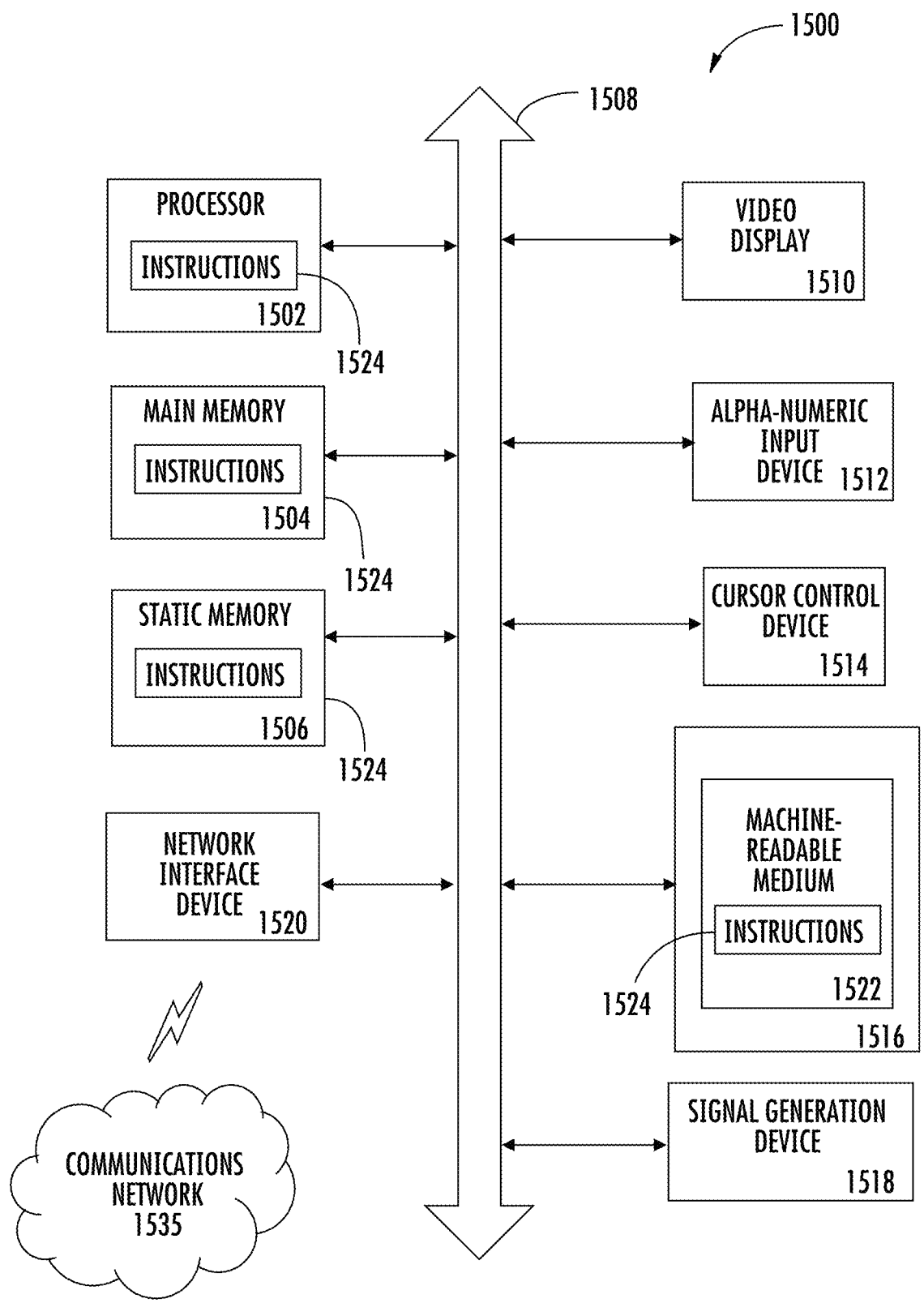
FIG. 15 illustrates a schematic diagram of a machine in the form of a computer system within which a set of instructions, when executed, may cause the machine to perform any one or more of the methodologies or operations associated with a wireless tattoo machine.

Referring now also to FIG. 15, at least a portion of the methodologies and techniques described with respect to the exemplary embodiments of the tattoo machine 1 and other embodiments of the tattoo machine can incorporate and/or interact with a machine, such as, but not limited to, computer system 1500, or other computing device within which a set of instructions, when executed, may cause the machine to perform any one or more of the methodologies or functions discussed above. The machine may be configured to facilitate various operations conducted by the tattoo machine 1 and other embodiments of the tattoo machine disclosed herein. For example, the machine may be configured to, but is not limited to, assist the tattoo machine 1 by providing processing power to assist with processing loads experienced in the tattoo machine 1, by providing storage capacity for storing instructions for or data associated with the tattoo machine 1, or by assisting with any other operations conducted by or within the tattoo machine 1 and/or other tattoo machines described in the present disclosure. As further examples, the machine may assist with processing and storing information associated with the state of the tattoo machine 1, voltage setting information, battery life information, sensor data obtained via sensors of the tattoo machine 1, information associated with the components of the tattoo machine 1, information associated with the tattoo machine's 1 operation in a given tattoo session, information associated with shocks or impacts experienced by the tattoo machine 1, any information associated with operational parameters associated with the tattoo machine 1, temperature information associated with the tattoo machine 1, location information for the tattoo machine 1, information associated with the duration of operation of the tattoo machine 1, information associated with the mobile device 2000, information associated with the foot switch 4000, any other information generated according to the present disclosure, or a combination thereof, information relating to the client receiving the tattoo, including name, session time, time and date of the session, type or name of service being performed.

In some embodiments, the machine may operate as a standalone device. In some embodiments, the machine may be connected (e.g., using communications network 1535, another network, or a combination thereof) to and assist with operations performed by other machines and systems, such as, but not limited to, the tattoo machine 1, other tattoo machines disclosed herein, the mobile device 2000, footswitch 4000, any components described in the present disclosure, any other system, program, component and/or device, or any combination thereof. The machine may be connected with any component of the tattoo machine 1. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1500 may include a processor 1502 (e.g., a central processing unit (CPU), a graphics processing unit (GPU, or both), a main memory 1504 and a static memory 1506, which communicate with each other via a bus 1508. The computer system 1500 may further include a video display unit 1510, which may be, but is not limited to, a liquid crystal display (LCD), a flat panel, a solid state display, or a cathode ray tube (CRT). The computer system 1500 may include an input device 1512, such as, but not limited to, a keyboard, a cursor control device 1514, such as, but not limited to, a mouse, a disk drive unit 1516, a signal generation device 1518, such as, but not limited to, a speaker or remote control, and a network interface device 1520.

The disk drive unit 1516 may include a machine-readable medium 1522 on which is stored one or more sets of instructions 1524, such as, but not limited to, software embodying any one or more of the methodologies or functions described herein, including those methods illustrated above. The instructions 1524 may also reside, completely or at least partially, within the main memory 1504, the static memory 1506, or within the processor 1502, or a combination thereof, during execution thereof by the computer system 1500. The main memory 1504 and the processor 1502 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 1522 containing instructions 1524 so that a device (e.g. tattoo machine 1) connected to the communications network 1535, another network, or a combination thereof, can send or receive voice, video or data, and communicate over the communications network 1535, another network, or a combination thereof, using the instructions. The instructions 1524 may further be transmitted or received over the communications network 1535, another network, or a combination thereof, via the network interface device 1520.

While the machine-readable medium 1522 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other rewritable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

In light of the foregoing description, it should be recognized that embodiments in accordance with the present disclosure can be realized in numerous configurations contemplated to be within the scope and spirit of the claims. The description and its embodiments are not limitations on the scope of the disclosure, and this disclosure encompasses modifications, and equivalent features and structures.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Except as specifically defined herein, all technical and scientific terms used herein are to be given as broad a commonly understood meaning as possible while maintaining claim validity.

What is claimed:

1. A wireless tattoo machine comprising:
    a motor housing having an exterior, the exterior having a motor housing perimeter defining a central axis;
    a motor constrained within an interior portion of the motor housing, the motor having a driveshaft with an axis of rotation of oriented substantially orthogonal to the central axis;
    a motion translation assembly dimensioned to fit within the motor housing comprising a cam disk having a cam aperture and an outer cam circumference defining a cam center, the cam aperture being offset a distance from the cam center and dimensioned to accept the driveshaft, whereby the driveshaft rotatably engages the cam disk;
    a connecting arm having a first end and a second end, the second end having an opening defining an inner arm circumference, wherein a portion of the cam disk overlays a surface of the second end of the connecting arm, which is opposite the motor, such that the second end of the connecting arm is sandwiched between the portion of the cam disk and the motor; and
    a bearing provided between the outer cam circumference and the inner arm circumference; and
    a detachable power supply unit, a housing of the detachable power supply unit adapted to reversibly couple to the motor housing rotatably about the central axis, wherein the detachable power supply powers the motor without connection to an external power source.

2. The wireless tattoo machine of claim 1, wherein a diameter of the motor housing is between approximately 7 millimeters and approximately 45 millimeters.

3. The wireless tattoo machine apparatus of claim 1, wherein the motor housing further comprises a forward housing end and a rearward housing end, and wherein the motion translation assembly further comprises a motor tray dimensioned to be insertedly constrained within the motor housing, the motor tray having a mounting portion for securing the motor.

4. The wireless tattoo machine of claim 3, wherein the motion translation assembly further comprises a drive pin, and wherein the motor tray further includes a slide cylinder portion, the drive pin slidingly constrained within a hollow of the slide cylinder portion and coupled to the first end of the connecting arm, whereby the motion translation assembly translates rotational motion produced by the motor into rectilinear oscillating motion parallel with the central axis.

5. The wireless tattoo machine of claim 4, wherein the motor housing further includes a grip attachment portion, the grip attachment portion having an aperture dimensioned to slidably accept the slide cylinder portion of the motor tray.

6. The wireless tattoo machine of claim 5, further comprising a grip, the grip having substantially radial symmetry about the central axis and having a cartridge end and a motor housing mating portion distal to the cartridge end, the cartridge end dimensioned to accept a needle cartridge, the motor housing mating portion adapted to reversibly mate with the grip attachment portion of the motor housing.

7. The wireless tattoo machine of claim 6, further comprising:
    a ratchet disc having a slot and at least one positive detent, the ratchet disc configured to slottedly mate with the grip attachment portion; and
    the motor housing mating portion of the grip having at least one groove parallel to the central axis dimensioned to engage with the at least one positive detent; wherein the ratchet disc operatively interacts with the at least one groove as the grip is rotated about the central axis relative to the housing.

8. The wireless tattoo machine of claim 1, wherein the detachable power supply unit further includes a power controller, a charging port, a power terminal, a processor, memory, and at least one transceiver, the processor in electrical communication with the memory, the power controller, and the at least one transceiver, the power controller in electrical communication with a battery, the charging port, and the power terminal, whereby the processor receives a wireless signal from a control unit, stores data conveyed in the wireless signal in the memory, and controls voltage delivered from the battery through the power controller to the power terminal.

9. The wireless tattoo machine of claim 8, further comprising
    electrical circuitry constrained within the motor housing, the electrical circuitry configured to communicate wirelessly with a machine control unit and control an amount of direct current delivered to the power terminal.

10. A method of controlling the wireless tattoo machine of claim 1, comprising:
    generating, via a control device, a wireless control signal for controlling the wireless tattoo machine; and
    transmitting the wireless control signal from the control device to a communications device of the wireless tattoo machine, wherein the wireless control signal is utilized by the wireless tattoo machine to facilitate an operation of the wireless tattoo machine.

11. The method of claim 10, wherein the control device comprises a foot switch, a mobile device, or a combination thereof.

12. The method of claim 10, further comprising receiving a voice command from a user of the control device.

13. The method of claim 12, further comprising generating the wireless control signal based on the voice command.

14. The method of claim 10, further comprising generating another wireless control signal, and further comprising changing the operation of the wireless tattoo machine based on the another wireless control signal.

15. The wireless tattoo machine of claim 1, wherein the detachable power supply unit comprises:
    a battery;
    a communication device;
    a memory that stores instructions;
    a processor that executes the instructions from the memory to perform operations, the operations comprising:
    receiving a signal from a control device communicatively linked to the wireless tattoo machine; and
    controlling the wireless tattoo machine by utilizing the signal.

16. The wireless tattoo machine of claim 15, wherein the control device comprises a foot switch, a mobile device, a remote device, or a combination thereof.

17. The wireless tattoo machine of claim 15, wherein the battery pack further comprises a charging port charging the battery via a charging cord.

18. The wireless tattoo machine of claim 15, wherein the communication device comprises a wireless module, a wireless chip, a radio, a cellular device, or a combination thereof.

19. The wireless tattoo machine of claim 15, further comprising a speaker, an input button for controlling the tattoo wireless machine, a light emitting diode for outputting state information for the wireless tattoo machine, or a combination thereof.

20. The wireless tattoo machine of claim 15, further comprising a light source capable of producing a plurality of colors corresponding to voltage settings of the wireless tattoo machine.

\* \* \* \* \*